(12) United States Patent
Lipsky et al.

(10) Patent No.: US 6,203,793 B1
(45) Date of Patent: Mar. 20, 2001

(54) COMPOSITIONS AND METHODS FOR TREATING THERMAL INJURY

(75) Inventors: Peter Lipsky, Dallas; William Mileski, Richardson, both of TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 08/832,464

(22) Filed: Apr. 2, 1997

Related U.S. Application Data

(63) Continuation of application No. 07/843,112, filed on Feb. 28, 1992, now abandoned.

(51) Int. Cl.$^7$ .................................................. A61K 39/345
(52) U.S. Cl. ...................... 424/143.1; 424/130.1; 424/141.1; 424/144.1; 424/152.1; 424/153.1; 424/154.1; 424/156.1; 424/172.1; 424/173.1
(58) Field of Search ............................. 424/130.1, 141.1, 424/143.1, 144.1, 152.1, 153.1, 154.1, 156.1, 172.1, 173.1

(56) References Cited

U.S. PATENT DOCUMENTS

| 4,965,271 | 10/1990 | Mandell et al. . |
| 5,009,889 | 4/1991 | Taylor et al. . |
| 5,284,931 | * 2/1994 | Springer et al. . |

FOREIGN PATENT DOCUMENTS

| 0 314 863 A2 | 5/1989 | (EP) . |
| WO 86/00639 | 1/1986 | (WO) . |

OTHER PUBLICATIONS

Harlow et al (1991) West J. Med. 155: 365–369.*
Moore et al (1986) New Engl. J. Med. 314(15):948–953.*
Sugita et al (1986) Int. J. Cancer 37: 351–357.*
Greyonadis et al (1993) Trends in Biotech 11: 440–442.*
Hans et al (1993) Trends in Biotech. 11: 42–44.*
Thorpe (1993) Trends in Biotech. 11: 40–42.*
Geishon (1993) Nature 311: 290.*
Fitzer–Schiller (Jan. 19, 1993) The Washington Post, p. D3.*
Zawacki, B. S. In "The Art and Science of Burn Care" (J.A. Boswick et al, eds) Aspen Publishers, Rockville, MD, pp. 75–36.*
Roth (1991) "Essential Immunology", Blackwell Scientific Publications, Oxford, pp. 65–68–74.*
Kansas, "LAM–1: Structure, Function, Genetics and Evolution," Ch. 3 p. 31–59 Cellular and Molecular Mechanisms of Inflammation vol. 2, 1991.*
Albelda, The FASEB Journal vol. 8:504–512, May 1994.*
Mileski, et al., "Inhibition of Leukocyte–Endothelial Adherence Following Thermal Injury," The Association for Academic Surgery, Twenty–Fifth Annual Meeting, Colorado Springs, CO, Nov. 20–23, 1991.

Ward et al., (1990) The Journal of Trauma, 30(12) Supplement: 575–579, *Pathophysiologic Events Realted to Thermal Injury of Skin*.
Argenbright et al., (1991) Journal of Leukocyte Biology, 49:253–257, *Monoclonal Antibodies to the Leukocyte Membrane CD18 Glycoprotein Complex and to Intracellular Adhesion Molecule Inhibit Leukocyte Endothelial Adhesion in Rabbits*.
D'Alesandro et al., (1990) Journal of Burn Care and Rehabilitation, 11:295–300, *Quantitative and Functional Alterations of Peripheral Blood Neutrophils After 10% and 30% Thermal Injury*.
Mileski et al., (1992) J. Surg. Res., 52:334–339, *Inhibition of Leukocyte–Endothelial Adherence Following Thermal Injury*.
Holcroft, J., (1991) pp. 34–57, In: Textbook of Surgery, Sabiston et al., eds., 4th ed. *Shock, Causes and Management of Circulatory Collapse*.
Mileski et al., (1993), Am. Phys. Soc., 74(3) :1432–1436, *Inhibition of Leukocyte Adherence and Aggregation for Treatment of Severe Cold Injury to Rabbits*.
Weiss et al., (1989) N. Engl. J. Med., 320:365, *Tissue Destruction by Neutrophils*.
Champlin, R. (1991) McGraw–Hill 12:1552–1561, In: Harrison's Principles of Internal Medicine, *The Leukemias*.
Luterman et al., (1987) J. Boswick, ed. pp. 233–253, The Art and Science of Burn Injury, *Chemical Burn Injury*.
Daum et al., (1987) In: Cryobiology 24:65–73, *Vascular Casts Dmeonstrate Microcirculatory Insufficiency in Acute Frostbite*.
Bourne et al., (1986) J. Surg. Res. 40:26–35, *Analysis of Microvascular Changes in Frostbite Injury*.
McCauley et al., (1983) J. of Trauma 23(2):143–147, *Frostbite Injuries: A Rational Approach Based on the Pathophysiology*.
Hansbrough et al., (1990) J. of Trauma 30(6):671–675, *Postburn Immune Suppression: An Inflammatory Response to the Burn Wound?*.

(List continued on next page.)

*Primary Examiner*—Anthony C. Caputa
*Assistant Examiner*—Anne L. Holleran
(74) *Attorney, Agent, or Firm*—Niro, Scavone, Haller & Niro

(57) ABSTRACT

Disclosed is a method for treating tissue necrosis (loss) in an animal. Tissue necrosis is treated by providing the subject with an anti-adhesion cell agent capable of binding an ICAM-1 antigen, a CD18 antigen, an L-selectin agent, a CD44 antigen, a P-selectin antigen, a VCAM-1 antigen, an ICAM-2 antigen, or a fragment thereof. Also provided is a method for preventing thermal-related tissue loss or necrosis, particularly the thermal injury and progressive tissue necrosis which results from a burn injury. Thermal-related tissue injury surrounding a thermal injury site is inhibited or prevented by providing an animal with an anti-adhesion agent, such as an anti-CD18 antibody, an anti-ICAM-1 antibody, or a mixture or fragment thereof. A method for inhibiting/preventing scarring attendant healing of a thermal injury is also disclosed.

47 Claims, 6 Drawing Sheets

OTHER PUBLICATIONS

Babcock et al., (1990) Clin. Immun. & Immunop. 54:117–125, *Flow Cytometric Analysis of Neutrophil Subsets in Thermally Injured Patients Developing Infection.*

Spagnuolo et al., (1992) J. of Surg. Res. 53:211–217, *Fibronectin Binding and Neutrophil Aggregation in Burn Injury.*

Solomkin et al., (1990) J. of Trauma 30(12) :S80–S85, *Neutrophil Disorders in Burn Injury: Complement, Cytokines, and Organ Injury.*

Friedl et al., (1989) Am. J. Path., 135(1) :203–217, *Roles of Histamine, Complement and Xanthine Oxidase in Thermal Injury of Skin.*

Harlan, J.M. (1987), Consequences of Leukocyte–Vessel Wall Interactions in Inflammatory and Immune Reactions., *Seminar in Thrombosis and Hemostasis*, 13(4):434–44.

Vedder, N.B. et al. (1988), A Monoclonal Antibody to the Adherence–promoting Leukocyte Glycoprotein, CD18, Reduces Organ Injury and Improves Survival from Hemorrhagic Shock and Resuscitation in Rabbits., *J. Clin. Invest.* 81:939–944.

Movat et al. (1987), Neutrophil Emigration and Microvascular Injury., *Patho. Immunopathol. Res.*, 6:153–176.

Weiss, S.J. (1989), Tissue Destruction by Neutrophils., *N. Engl. J. Med.*, 320:365–376.

Boykin et al. (1980), In Vivo Microcirculation of a Scald Burn and the Progression of Postburn Dermal Ischemia., *Plastic and Reconstructive Surgery*, 66(2):191–198.

Deitch et al. (1990), Effect of Local and Systemic Burn Microenvironment on Neutrophil Activation as Assessed by Complement Receptor Expression and Morphology., *J. Trama*, 30(3):259–268.

Price et al. (1987), In Vivo Inhibition of Neutrophil Function in the Rabbit Using Monoclonal Antibody to CD18., *J. Immunol.*, 139:4174–4177.

Pohlman et al. (1986), An Endothelial Cell Surface Factor(s) Induced In Vitro by Lipopolysaccharide, Interleukin 1,and Tumor Necrosis Factor–α Increases Neutrophil Adherence by a CDw18–Dependent Mechanism., *J. Immunol.*, 136:4548–4553.

Arfors et al. (1987), A Monoclonal Antibody to the Membrane Glycoprotein Complex CD18 Inhibits Polymorphonuclear Leukocyte Accumulation and Plasma Leakage In Vivo., *Blood*, 69(1):338–340.

Nelson et al. (1986), Influence of Minor Thermal Injury on Expression of Complement Receptor CR3 on Human Neutrophils., *AJP*, 125(3):563–570.

Zimmerman, G.A. and Mcintyre, T.M. (1988), Neutrophil Adherence to Human Endothelium In Vitro Occurs by CDw18 (Mol, MAC–1/LFA–1–1/GP 150,95) Glycoprotein–dependent and –independent Mechanisms., *J. Clin. Invest.*, 81:531–537.

Wallis et al. (1986), Monoclonal Antibody–Defined Functional Epitopes on the Adhesion–Promoting Glycoprotein Complex (CDw18) of Human Neutrophils., *Blood*, 67(4):1007–1013.

Smith et al. (1988), Recognition of an Endothelial Determinant for CD18–dependent Human Neutrophil Adherence and Transendothelial Migration., *J. Clin. Invest.*, 82:1746–1756.

Harlan et al. (1986), The Role of Neutrophil Membrane Proteins in Neutrophil Emigration., *Satellite Symp. 6th Int. Congr. Immunology*, 94–104.

Price et al. (1986), In Vivo Inhibition of Neutrophil Function Using Monoclonal Antibody to the CDw18 Complex., *Clinical Research*, 34(2):467A.

Barton et al. (1989), The effect of Anti–Intercellular Adhesion Molecule–1 on Phorbol–Ester–Induced Rabbit Lung Inflammation., *J. Immunol.*, 143:1278–1282.

Winn et al. (1991), Chapter—Administration of anti–adhesion molecules., *In: The Immune Consequences of Trauma, Shock and Sepsis. Mechanism and Therapeutic Approaches.*, Springer–Verlag.

Sharar et al. (1991), Chapter—The role of β–2 leukocyte integrins in vivo., *In: The Immune Consequences of Trauma, Shock and Sepsis. Mechanism and Therapeutic Approaches.*, Springer–Verlag.

Mileski et al. (1990), Inhibition of CD18–dependent neutrophil adherence reduces organ injury after hemorrhagic shock in primates., *Surgery*, 108:206–212.

Wegner et al. (1990), Intercellular Adhesion Molecule–1 (ICAM–1) in the Pathogenesis of Asthma., *Science*, 247:456–459.

Cosimi et al. (1990), In Vivo Effects of Monoclonal Antibody to ICAM–1 (CD54) in Nonhuman Primates with Renal Allografts., *J. Immunol.*, 144:4604–8.

Johnson, J.M. (1990) *In: Laser–Doppler Blood Flowmetry*, Shephard A.P. and Oberg P.A. Kluwer, Academic Publishers, Norwell, MA, pp. 121–139.

Schmidt–Schonbein, G.W. (1987), Capillary plugging by granulocytes and the no–reflow phenomenon in the microcirculation., *Fed. Proc.*, 46:2397–2401.

Andersen et al. (1985), The Severe and Moderate Phenotypes of Heritable Mac–1, LFA–1 Deficiency: Their Quantitative Definition and Relation to Leukocyte Dysfunction and Clinical Features., *J. Infect. Dis.*, 152:668–689.

Galfre et al. (1977), Antibodies to major histocompatibility antigens produced by hybrid cell lines., *Nature*, 266:550–552.

Remington's Pharmaceutical Sciences (1990) 18th ed., Osol., A., Ed., Mack, Easton, PA, pp. 1300–1303; pp. 1691–1693.

Dustin et al. (1986), Induction by IL 1 and Interferon–γ: Tissue Distribution, Biochemistry, and Function of a Natural Adherence Molecule (ICAM–1)., *J. Immunol.*, 137:245.

Alsbjörn et al. (1984), Laser Doppler Flowmetry Measurements of Superficial Dermal, Deep Dermal and Subdermal Burns., *Scand. J. Plast. Reconstr. Surg.*, 18:75–79.

Borgstrom et al., (1991) "Inhibition of Neutrophils (PMNs) Attenuates The Extension of tissue Destruction After Thermal Injury," *Surgical Forum*, vol. XLII, pp. 614–617.

\* cited by examiner

COMPOSITIONS AND METHODS FOR TREATING THERMAL INJURY

This is a continuation of application Ser. No. 07/843,112, filed Feb. 28, 1992 now abandoned.

BACKGROUND OF THE INVENTION

1. Field of the Invention

The present invention relates to the role of inflammatory cells in the extension of tissue necrosis surrounding a thermally injured tissue. The invention also relates to the field of therapeutic agents and methods for the prevention and inhibition of tissue necrosis incident thermal injury in an animal.

2. Description of the Related Art

Thermal injuries result in a cascade of events which initially produces an area of irreversible tissue destruction surrounded by a marginal zone of injury with reduced blood flow. The marginal zone of injury is referred to as a "zone of stasis". This "zone of stasis" is recognized as being at high risk of progressive tissue destruction. Particularly, during the post-injury period, the zone of stasis is subject to a progressive extension of the area of tissue loss (necrosis) surrounding the initially tissue damaged site.

The progression of tissue loss is due in part to microvascular damage at and around the injured site. Three cellular events are primarily responsible for this observed microvascular damage. These include:

1) The adherence of neutrophils (polymorphonuclear neutrophils, PMNs) to capillary endothelial cells (EC), which induces the release of products toxic to host tissue;

2) The aggregation of neutrophils, which causes clogging of capillaries and post-capillary venules; and 3) The local activation of neutrophils to produce mediators of tissue damage (nitric oxide, etc.).

The present invention provides for inhibiting the progressive tissue destruction typical of post-thermally injured patients through methods which inhibit each of these cellular events.

Leukocytes, particularly neutrophils, are central mediators of microvascular endothelial injury in many acute pathologic processes.[1-4] Leukocytes, particularly polymorphonuclear neutrophils (PMNs), monocytes and lymphocytes may be characterized as inflammatory cells, as cells of these cell types play some role in the inflammatory response.[1]

Polymorphonuclear neutrophils are known to play a central role in inflammatory responses of many types. During inflammation, PMN-EC adherence results in the formation of a microenvironment between the PMN and the EC where PMN derived proteases (such as serine proteinase, elastase, collagenase and gelatinase), and toxic oxygen products produced by both the EC and PMN (such as superoxide anion, hydrogen peroxide and the hydroxyl radical), exist in high local concentrations.[1] These highly reactive substances, partially protected from inactivation by circulating plasma anti-proteases and free radical scavengers, then produce endothelial cell injury. This endothelial cell injury in turn results in intercellular gap formation, increased microvascular permeability, hemorrhage, edema and thrombosis.

PMN—PMN aggregation also occurs during inflammation, and further compromises the microvascular circulation by obstructing capillaries and post-capillary venules, thereby extending the zone of ischemia at the injury site. Because neutrophils (PMN's, particularly) are larger and less deformable than erythrocytes, they may plug small capillaries as perfusion pressure drops. Such a condition results in a mechanism of microvascular injury referred to as microvascular occlusion during ischemia-reperfusion.[2]

PMNs have been shown to be activated during burn injury but their exact role as contributors to both the systemic and local microvascular occlusion seen following burn injury remains to be completely delineated. For example, Deitch et al. observed an increase in PMN activation when PMNs are exposed to burn blister fluid in vitro, including an increase in PMN complement receptor type 3 (CR3) expression.[6] Solem et al. have demonstrated an increase in the surface expression of a neutrophil membrane glycoprotein complex (CD18) on circulating PMNs following burn injury.[7]

Several receptor-counter receptor pairs of ligands on the PMN and the EC have also been identified. One of the major receptor pairs is the neutrophil membrane glycoprotein complex, CD11–CD18 and its natural binding ligand, the intercellular adhesion complex (ICAM-1, CD54) on endothelial cells. The CD11/CD18 complex is a heterodimer composed of three distinct alpha chains CD11a, CD11b, and CD11c with a common beta chain, CD18. The CD11/CD18 complex, is present constitutively on the surface of normal neutrophils. The activity of the CD11/CD18 complex is upregulated in response to appropriate stimuli, such as to activated complement fragment 5a (c5a) or bacterial endotoxin.

ICAM-1 is a 76–97 kD glycoprotein (not a heterodimer) present on the endothelial cell (EC). Its expression by EC is upregulated by a number of inflammatory cytokines, including IL-1 and interferon.[24]

It is known that neutrophil-endothelial cell adherence results from the specific interaction of the CD18 complex with ICAM-1. Monoclonal antibodies to portions of the CD11/CD18 complex have been found to functionally inhibit neutrophil aggregation and PMN-EC adherence in vitro and in vivo.[1,6-10] One such antibody, R 15.7, is a murine derived IgG2a which recognizes a functional epitope on CD18.[11] R 15.7 has been demonstrated both in vitro and in vivo to effectively block neutrophil adherence and emigration to a variety of stimuli, including LPS, phorbol myristate acetate (PMA), N-formylmethionyl-leucyl-phenylalanine (FMLP), complement fragment 5a (C5a), leukotriene B4 (LTB4), interleukin-1 (IL-1), and tumor necrosis factor (TNF).

Anti-CD18 antibodies have been shown to protect against inflammation by inhibiting PMN-EC adherence in reported isolated myocardial and intestinal ischemia-reperfusion injury studies.[12-13] Improved survival and reduced organ injury following hemorrhagic shock in rabbits and in non-human primates treated with anti-CD18 antibody have also been reported.[14]

The interaction of PMN-EC has also been modulated through the use of antibodies directed against the endothelial cell, particularly ICAM-1 in modulating inflammation. One such antibody, R 6.5, (ATCC #HB9580) is a murine-derived IgG2a.[20] Administration of R 6.5 has been reported to reduce in vivo PMN migration in experimental rabbit models of airway inflammation. Such treatment reportedly was effective in preventing and treating acute renal rejection in nonhuman primates.[15-16] These antibodies have also been described as inhibiting intercellular adhesion of cells of granulocyte or macrophage lineage.

ICAM-1 expression is upregulated by cytokines. Therefore, it appears to be important at sites of inflammation therapy in giving specificity. However, so far, there have been no beneficial consequences reported in regard to vascular tissue or the containment of tissue necrosis upon treatment with various antibody preparations.

While progression of tissue necrosis continues to be a significant pathology attendant thermal injury in patients, no specific methods have yet been developed to treat/inhibit this type of secondary tissue loss. Moreover, the molecular mechanisms which play a part in this type of progressive tissue necrosis still have not been well defined.

Discovery of a method to contain the process of progressive tissue damage would provide for the development of improved methods for managing the burn or other thermally injured patient. Secondary tissue loss attendant burn injury contributes to the severity of the thermal injury, as well as to the overall disability, disfigurement and mortality risks observed in patients suffering from serious thermal injury. Therefore, methods for inhibiting and/or preventing tissue necrosis progression would also improve the ultimate prognosis of the thermally injured patient.

SUMMARY OF THE INVENTION

The present invention relates to methods for treating and inhibiting thermal-injury related tissue necrosis in an animal. Virtually any thermal injury which results in tissue damage in the animal may be treated with the described therapeutic agents and methods. Most specifically, the present invention provides a method which may effectively reduce and/or prevent the tissue necrosis which occurs in tissue areas adjacent a thermally-damaged area, such as skin, through providing the animal with an anti-inflammatory cell agent capable of preventing the progression of molecular and physiological events which contribute to thermal-related secondary tissue loss.

The present invention utilizes the inventors novel observation that inflammatory cells, such as polymorphonuclear neutrophils (PMN's), are involved in causing the progression and extension of tissue necrosis surrounding a thermally injured site. The inventors were able to demonstrate that the progression of tissue necrosis surrounding, for example, a skin burn site could be inhibited by administering to an animal an agent which inhibited PMN's and/or an agent which inhibited the adhesion of PMN's to endothelial cell surfaces. This finding was most surprising, as previously, the role of PMN's and other "inflammatory cells" had been confined to inflammatory diseases and the physiological responses which occur during inflammation.

As will be appreciated, tissue inflammation is quite distinct from tissue death and necrosis. Inflammation relates to a localized protective response, while tissue necrosis is characterized by cell and tissue death. Therefore, the discovery that inflammatory cells, such as PMN's, were involved in tissue necrosis was most unexpected.

In one preferred embodiment of the invention, a method for inhibiting tissue necrosis in an animal is provided. This method comprises treating the animal with a therapeutically effective amount of an agent capable of binding to an antigen on an inflammatory cell or an antigen present on an endothelial cell For example, such agents include antibodies to CD18 antigen, ICAM-1 antigen, or fragments thereof, together in a pharmaceutically acceptable carrier solution (such as a Ringers solution), and may be administered to an animal having a thermal injury to provide for the treatment and/or inhibition of thermal injury related tissue necrosis.

Accordingly, particular antibodies and monoclonal antibodies themselves do not constitute the invention. Instead, the instant invention relates to the discovery that inflammatory cells play an important role in the extension, or progression, of burn injury. This particular discovery was made following the inventors' observation that antibodies to CD18 or ICAM-1, which are antigens on the surface of inflammatory cells or endothelial cells effectively prevented the extension of tissue necrosis surrounding a primary burn injury in an animal (see Example 4). Therefore, the described methods for treating an animal for burn injuries, primarily to effect a reduction in the ultimate tissue damage which occurs around, both laterally and vertically at an initial burn site, includes the use of that group of biologically active molecules which are capable of binding an inflammatory cell, such as a PMN, a monocyte, a leukocyte, or to those types of cells which interact by adherence to inflammatory cells, such as endothelial cells.

In one embodiment, the method for inhibiting tissue necrosis comprises administering a blocking or anti-adhesion agent to the animal. By way of example, the "blocking", "binding" or "anti-adhesion cell" agents of the invention include antibodies having binding affinity for an antigen, or a fragment of an antigen, present on an inflammatory cell or on an endothelial cell. By way of example, such agents include antibodies to CD18 antigen or antibodies to the ICAM-1 antigens. Any antibody having binding affinity for these particular antigenic species on neutrophils or endothelial cells, or any of the other adhesion molecules or antigenic species present on the surfaces of endothelial cells or neutrophils, would therefore affect the binding of inflammatory cells and the desired effect of containing the progression of tissue injury. The "binding" of the inflammatory cells will thus prevent the influx of neutrophils, primarily polymorphonuclear neutrophils, (one type of inflammatory cell) to a burn site. However, other endothelial cell or inflammatory cell adhesion molecules or antigens apart from or in addition to CD18 and ICAM-1 can be used to develop anti-adhesion agents (e.g., antibodies) to inhibit tissue necrosis spread and progression with equal efficacy.

For purposes of the described method, where the agent capable of binding an inflammatory cell is an antibody, the antibody may be either a monoclonal antibody or a polyclonal antibody. In a most preferred aspect of the invention, the antibody is directed against a CD11, CD18 or an ICAM-1 antigen. The CD18 antigen is characteristic of the cell membrane of polymorphonuclear neutrophils and other blood cells. However, many other antigenic species exist on the surface of inflammatory cells which may be used to generate antibodies for use in the present invention. Most preferably, the antibody is a monoclonal antibody.

The preferred antibody is a monoclonal antibody specific for the CD18 antigen or the ICAM-1 antigen. One example of a most preferred antibody of this type is the monoclonal antibody R 15.7 or R 6.5 (ATCC #HB9508).

Where the particular anti-adhesive cell molecule selected for the inhibition of tissue necrosis is a monoclonal antibody R 15.7 or R 6.5, the therapeutically effective amount of the antibody most preferred is between 1 mg/kg to about 10 mg/kg. Even more particularly, the most preferred dose of monoclonal antibody which constitutes a therapeutically effective amount is between 2 mg/kg to about 5 mg/kg.

The described therapeutic method may be used in the treatment of any animal, and may be particularly useful in the treatment of humans for containing and preventing tissue loss at tissues surrounding a thermal injury, involving the immediately surrounding tissue and deeper layers of the dermis and subdermal structures. The most preferred application of the present methods will be found in the treatment and containment of tissue necrosis surrounding a burn injury, such as a thermal injury resulting from skin contact with elevated temperatures. By way of example, such may constitute contact as with a heated element of greater than 50° C. such as a heated stove, etc.

The term "thermal-related tissue injury" as used in the description of the present invention is defined as tissue damage resultant from exposure of a tissue to heat, cold, electricity, chemicals, radiation, and the like. By way of example, heat-related thermal tissue injury may result from exposure to a hot (e.g., 100° C.) liquid (water, oil, etc.), gas, or object (machinery, iron, probe, etc.). By way of example, heated liquid-inflicted injury may include that resulting from exposure to scalding water, boiling oil, industrial lubricants, etc. Heated surfaces may include, for example, probes, machinery (specifically industrial machinery), or household items (iron, cooking utensils, stoves, etc.). A thermal-related injury may also encompass an injury inflicted by electrical heat, such as burns inflicted by electrical wires, telephone wires, circuit breaker boxes, electric stove lighting and the like.

In that tissue injury resulting from electricity is the result of electrical energy being converted to heat, the presently disclosed thermal injury protocol may also be used to treat persons suffering from either a high voltage (1000 volts) or low voltage (less than 1000 volts) electrical injury. Charring commonly occurs at the contact sites, and may also be produced by arching of current across flexor surfaces of joints. Apart from direct contact with a household or industrial electrical source, electrical thermal injury may also result from lightening injuries. Lightening is defined as a direct current of 100,000 or more volts and up to 200,000 amps.

Examples of thermal injury resulting from cold include that attendant the exposure of tissue to temperatures below 20° C. Heat or cold exposure sufficient to precipitate an area of tissue destruction are contemplated as within the scope of thermal injuries intended as treatable according to the methods and compositions of the present invention.

Chemical burns, such as those attendant exposure to acids and other caustic materials, as well as highly alkaline materials, may also be treated according to the disclosed methods to prevent necrotic tissue progression to areas surrounding the injury (i.e. zone of stasis). The burns which result from prolonged contact with petroleum agents, such as gasoline or diesel fuel (not flame burns) may also be treated according to the methods proposed herein. By way of example, prolonged contact with heated gasoline or diesel fuel is known to manifest full thickness (third degree) burns.

The size and severity of a thermal injury will vary depending on the type of agent and the duration exposure to the agent which caused the burn. For example, a skin burn resulting from exposure to boiling oil would be expected to be more severe, both in terms of tissue destruction and surface area of the burn, as compared to a skin burn inflicted by a brass probe heated to 100° C., or boiling water. However, regardless of the particular agent which precipitates the thermally-compromised (burned) skin area, treatment according to the herein disclosed methods would be expected to be equally as efficacious.

Thermal injury the result of exposure to heat are most specifically defined as those tissue injuries which result from the exposure of an animal to objects or substances heated to a temperature of greater than 50° C. (greater than 104° F.). The extent of tissue destruction will increase as a function of the length of exposure time to the elevated temperature. Human tissue can tolerate temperatures of 45–50° C. for relatively long periods of time without apparent injury.

As used in the description of the present invention, the term, "zone of stasis" is defined as a tissue area surrounding a thermal-damaged tissue, such as that peripheral skin area which surrounds a burn contact site. The zone of stasis typically is characterized by progressive impairment of the microvasculature, and therefore impaired blood flow. "Marginal zone" is used interchangeably with the term zone of stasis in the description of the present invention. The "marginal zone" is not characterized by complete tissue destruction, and often displays a redness and sensitivity to touch. This marginal region is also at risk of progressive tissue necrosis subsequent a thermal injury.

The term, "anti-adhesive cell molecule" is defined for purposes of describing the present invention, as a biological molecule which has binding affinity for adhesion cell receptors, such as to the CD18 cell receptor antigen of PMN's and other blood cells, or to the ICAM-1 cell receptor antigen of endothelial cells. The term "anti-inflammatory cell molecule" is used interchangeably with the term "anti-adhesive cell molecule" in the description of the present invention. These agents have been found by the present inventors to effectively reduce the progression of tissue necrosis by, in part, reducing microvascular occlusion at tissues surrounding the thermally damaged tissue site. By way of example, such anti-adhesive cell ("anti-inflammatory cell") molecules may include antibodies, both monoclonal and polyclonal.

In still another aspect of the present invention, a method for inhibiting tissue necrosis in a tissue area surrounding a burn in an animal is provided. In one embodiment, the method comprises measuring the tissue necrosis within one hour of a burn to provide a reference burn size, treating the animal with a therapeutically effective amount of a molecule capable of binding an ICAM-1 antigen, a CD18 antigen, an L-selectin antigen, a CD44 antigen, a VLA-4 antigen, or P-selectin antigen, an E-selectin antigen, a VCAM-1 antigen or an ICAM-2 antigen, or a fragment thereof, continuing to treat the animal with the molecule for not more than 24 hours after the burn contact, measuring the tissue necrosis surrounding the burn to provide a treatment burn size, and inhibiting tissue necrosis where the reference burn size is the same as the treatment burn size.

The present invention also most specifically provides a method for inhibiting progressive tissue necrosis at a thermal skin injury in an animal. The method comprises measuring the lateral area of the tissue necrosis at the thermal skin injury a first time to provide a reference skin necrosis size, treating the animal with a therapeutically effective amount of an anti-adhesive (anti-inflammatory cell) molecule capable of binding an ICAM-1 antigen, a CD18 antigen, an L-selectin antigen, a CD44 antigen, a VLA-4 antigen, a P-selectin antigen, an E-selectin antigen, a VCAM-1 antigen, an ICAM-2 antigen or a fragment thereof, measuring the lateral area of the tissue necrosis of the thermal injury a second time to provide a treated skin necrosis size, and comparing the reference size to the treated size of tissue necrosis, wherein a treated size equal to the reference size indicates an inhibition of the progression of tissue necrosis.

In a most preferred embodiment of the afore-described methods, the molecule is capable of binding to an ICAM-1 antigen, a CD18 antigen, or a fragment thereof, and is defined as an antibody. The antibody may be either a polyclonal antibody or a monoclonal antibody. Where the antibody selected is a monoclonal antibody capable of binding a CD18 antigen or a fragment thereof, the antibody may comprise R 15.7. Where the antibody is a monoclonal antibody capable of binding to a ICAM-1 antigen or a fragment thereof, the monoclonal antibody may comprise the R 6.5 monoclonal antibody.

The therapeutically effective amount of monoclonal antibody most preferred in the described method for inhibiting tissue necrosis and the progression of tissue necrosis (such as around a skin burn injury) is between about 1 mg/kg and about 10 mg/kg. Even more particularly, the therapeutically effective amount of monoclonal antibody constitutes a dose of between about 1 mg/kg and about 5 mg/kg. The most preferred therapeutically effective amount of monoclonal antibody to be used in the presently described method is about 2 mg/kg of the anti-ICAM-1 antibody produced by HB 9580, R 6.5. The most preferred dose of monoclonal antibody directed against CD18 antigen, R 15.7, is about 1 mg/kg.

It is expected that the anti-ICAM-1 or the anti- CD18 antibodies, either alone or in combination, would be equally efficacious in inhibiting tissue necrosis at a thermal injury site.

While the most preferred of mode of administering the anti-adhesion cell (anti-inflammatory cell) agents of the present invention is by intravenous injection, other modes of administration may be used with equal efficacy. For example, the described agents and preparations of the present invention may be administered to patients topically, intravenously, intramuscularly, subcutaneously, enterally or parenterally. The anti-adhesion cell agent of the present invention may be administered to an animal by injection as either a continuous infusion or by a single bolus injection. Most preferably, the agent will be administered as a single bolus injection at a dose of between about 1 mg/kg and about 5 mg/kg.

It is also expected that the presently disclosed methods will be effective for decreasing scarring or the formation of scar tissue attendant the healing process at a burn site. Scarring of tissue, or the formation of scar tissue, is defined as the formation of fibrous tissue at sites where normal tissue has been destroyed. The present invention therefore also proposes a method for decreasing scarring, specifically at skin tissue areas of second or third degree burn. This method may comprise first identifying an animal having a second or third degree burn and treating the animal with a therapeutically effective amount of a pharmaceutically acceptable preparation containing an agent capable of binding to a CD18 antigen, an ICAM-1 antigen, an L-selectin antigen, a CD44 antigen, a VLA-4 antigen, a P-selectin antigen, an E-selectin antigen, a VCAM-1 antigen an ICAM-2 antigen, or a fragment thereof, to decrease tissue scarring in the animal. A therapeutically effective amount of an agent for inhibiting scarring would be between about 1 mg/kg and about 10 mg/kg. The most preferred doses of between about 1 mg/kg and about 5 mg/kg are expected to be especially efficacious. Examples of an anti-inflammatory cell agent and an anti-endothelial cell agent which may be used for decreasing the formation of scar tissue are an anti-CD18 antibody, or an anti-ICAM-1 or anti-ICAM-2 antibody respectively. A mixture of these antibodies may be employed for this method in a most preferred aspect of the practice of the present invention.

It is contemplated that the proposed method would provide for an effective means of reducing scarring in animals, including rabbits and humans. By way of example, the agent may include an antibody. Either a monoclonal antibody or a polyclonal antibody, or a mixture thereof, may be used in the scar-decreasing treatment. Monoclonal antibodies most preferred for this use include the anti-ICAM-1 monoclonal antibody an anti-ICAM-2 antibody or the anti-CD18 monoclonal antibody. By way of example, such an anti-ICAM-1 antibody is a monoclonal antibody R 6.5 produced by the hybridoma ATCC HB 9580. The monoclonal antibody specific for CD18 antigen, R 15.7, is stored in the inventors laboratory.

As the particular CD18 or ICAM-1 receptors themselves are not critical to providing the described methods of treatment, other antibodies, both monoclonal and polyclonal, which are capable of binding other inflammatory cell antigens may be employed with equal efficacy in the practice of the present invention. For example, antibodies having binding affinity or monocytes, macrophages, lymphocytes (both B and T lymphocytes), cytotoxic T lymphocytes), and other cell types involved in the inflammatory process, may be employed in the present invention. Of particular interest would be antibodies to adhesion molecules on inflammatory cells including L-selectin, CD44 and VLA-4 and adhesion molecules on endothelial cells including P-selectin, E-selectin, VCAM-1 and ICAM-2, among others.

Antibodies to a particular inflammatory cell may be prepared according to standard protocols known to those of skill in the art.

In still another aspect of the invention, a method for inhibiting the progression of polymorphonuclear neutrophil-mediated and endothelial cell mediated tissue necrosis at a skin burn site in an animal is provided. This method comprises treating the animal with a therapeutically effective amount of an agent capable of binding an ICAM-1 antigen, CD18 antigen, L-selectin, CD44, VLA-4, P-selectin, E-selectin, VCAM-1, ICAM-2, or a fragment thereof, together in a pharmaco-logically acceptable carrier solution; such as a Ringers solution. The agent used as a therapeutic agent may be a mixture of any of the aforelisted agents but most preferably is a mixture of an anti-ICAM-1 antibody and an anti-CD18 antibody or either of these antibodies individually. Either a polyclonal or monoclonal antibody having the described binding affinities is expected to provide the same anti-tissue necrotic effect according to the claimed method. Where the antibody is a monoclonal antibody, such monoclonal antibodies include by way of example the R 6.5 monoclonal antibody, which is specific for ICAM-1 antigen, and the R 15.7 monoclonal antibody, which is specific for the CD18 antigen.

While the claimed method will provide for the inhibition of tissue necrosis when administered within 48 hours of the burn, enhanced inhibition of tissue necrosis may be obtained by administering the described therapeutic agent(s) to the animal within between three to six hours of the thermal injury. An even greater anti-tissue necrotic effect may be obtained upon administering the described antibody or antibodies within one hour of the thermal injury.

According to the above-described method, a therapeutically effective amount of a mixture of the anti-ICAM-1 antibody and the anti-CD18 antibody includes between about 1 mg/kg to about 3 mg/kg of the anti-ICAM-1 antibody and between about 1 mg/kg to about 3 mg/kg of the anti-CD18 antibody. In addition, the inventors have observed that a preparation of a single anti-ICAM-1 antibody or an anti-CD18 antibody is equally efficacious in inhibiting the progression of polymorphonuclear neutrophil-mediated tissue necrosis at a skin burn site. Therefore, the method may also employ a preparation which includes only one of these antibody agents. The agent may be administered to the animal according to any of the routines described herein.

The inventors demonstrate that the above-described method provides an effective reduction in the progression of tissue necrosis surrounding a burn site in a mammal, such as the rabbit. Therefore, it is contemplated that the herein-described methods would be equally efficacious in the treatment of thermal related injuries, particularly heat inflicted tissue injuries, in humans. Particular dosages and schedules of treatment for humans may be defined employing the herein-described therapeutic agents according to methods known to those of ordinary skill in the medical arts, given the results and teachings of the present disclosure.

The following abbreviations are used throughout the description of the present invention.

PMN=polymorphonuclear neutrophil
EC=endothelial cell
CR3=complement receptor type 3
PMA=phorbol myristate acetate
Hct=hematocrit
BF=blood flow
WBC=white blood cell
CD11/CD18=a neutrophil membrane glycoprotein complex
R 15.7=a monoclonal antibody to CD18
R 6.5=a monoclonal antibody to ICAM-1
ICAM-1=an endothelial cell intercellular adhesion molecule

DETAILED DESCRIPTION OF THE PREFERRED EMBODIMENTS

Figure 1:
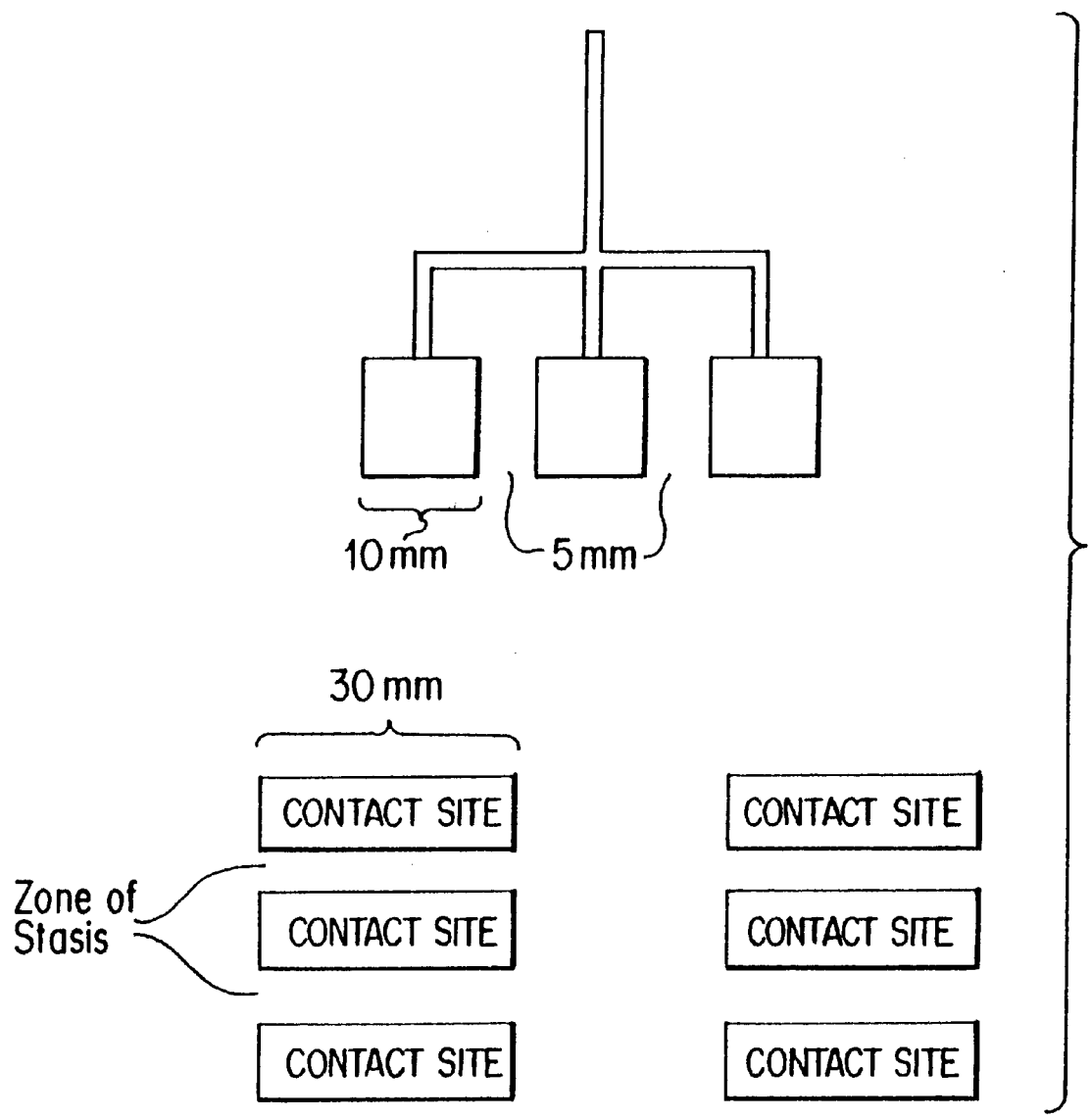
FIG. 1—Illustration of the dimensions and relative positions of burn contact site, zones of stasis and unburned skin sites or New Zealand white rabbits.

The invention provides an effective therapeutic regimen for the treatment and inhibition of tissue necrosis in vivo. Specifically, methods for reducing and inhibiting tissue necrosis tissues compromised by thermal injury, such as burns, are disclosed, as well as methods for reducing scarring in an animal. The presently disclosed techniques may be employed as both a pretreatment and a post-injury treatment to inhibit tissue necrosis at a thermal injury site.

Thermal injury for purposes of the present invention includes tissue damage resulting from heat ($\geq 50°$ C.), cold ($\leq 35°$ C.), electrical or chemical contact with a tissue.

The methods of the present invention employ agents capable of binding a CD18 antigen, an ICAM-1 antigen, an L-selectin antigen, a CD44 antigen, a VLA-4 antigen, a P-selectin antigen, an E-selectin antigen, a VCAM-1 antigen, an ICAM-1 antigen, or a fragment or combination thereof. Most preferably, the agent is an antibody. The antibodies of choice are monoclonal antibodies. By way of example, such monoclonal antibodies suitable for use in the present invention include the antibody produced by hybridoma clone R 15.7 or clone R 6.5. These antibodies have been found by the present inventors to constitute very effective therapeutic agents for the described methods.

The particular antibodies of the present invention include also any fragment of the above-described antibodies which is capable of binding to the ICAM-1 antigen, the CD18 antigen an L-selectin antigen, a CD44 antigen VLA-4 antigen, a P-selectin antigen, an E-selectin antigen, a VCAM-1 antigen, an ICAM-1 antigen, or a fragment or combination thereof. Thus, the present invention extends to antibodies, both monoclonal and polyclonal, as well as biologically active fragments thereof, which are capable of binding any one of the enumerated antigens or complexes thereof such as the CD18 glycoprotein complex antigen. Such antibodies may be produced either by an animal, by tissue culture, by hybridoma, or by recombinant DNA techniques. The particular R 15.7 and R 6.5 designated hybridomas produce monoclonal antibodies which were prepared using hybridoma technology.

The present invention is intended to include the "functional derivatives" of the antibodies and other agents described herein. A "functional derivative" of, for example, an ICAM-1 antibody or a CD18 antibody is defined for purposes of describing the present invention as a compound which possesses a biological activity (either functional or structural) that is substantially similar to the biological activity of an ICAM-1 antibody or a CD18 complex antibody.

The term "functional derivative" is intended to include a fragment, variant, analog or chemical derivatives of a molecule. A "fragment" is meant to refer to any polypeptide subset of the molecule (i.e., an antibody). A "variant" of a molecule is meant to refer to a molecule substantially similar in structure and function to either the entire molecule, or a fragment thereof. A molecule is said to be "substantially similar" to another molecule if both molecules have substantially similar structures, or if both molecules possess a similar biological activity. Thus, provided that two molecules possess a similar activity, they are considered variants, as that term is used herein, even if one of the molecules contains, for example, additional amino acid residues not found in the other, or if the sequence of amino acid residues is not identical. An "analog" of a molecule is meant to refer to a molecule substantially similar in function to either the entire molecule or to a fragment thereof.

As used herein, a molecule is said to be a "chemical derivative" of another molecule when it contains additional chemical or biochemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of eliciting such effects are disclosed in Remington's *Pharmaceutical Sciences* (1980) $^{22}$, which reference is specifically incorporated herein by reference for this purpose.

It is contemplated that molecules which bind an ICAM-1 antigen, a CD18 antigen, an L-selectin antigen, a CD44 antigen, a VLA-4 antigen, a P-selectin antigen, an E-selectin antigen, a VCAM-1 antigen, an ICAM-1 antigen, or a fragment or combination thereof, may be used as both a pre- and post-thermal injury therapeutic agent in accordance with the present invention.

Since ICAM-1 and CD18 antigen are naturally expressed on the surfaces of some cells, such as endothelial cells and neutrophils, the introduction of the surface antigens expressed by either of the cell types into an appropriate animal, as by intraperitoneal injection, etc., will result in the production of antibodies capable of binding to the ICAM-1 antigen or to the CD18 antigen. If desired, the serum of such an animal may be removed and used as a source of polyclonal antibodies capable of binding to each of these antigens. It is, however, preferable to prepare a hybridoma cell line capable of producing one or the other specific monoclonal antibody. A hybridoma cell line may be prepared by removing splenocytes from an animal which has been treated with the specific antigen, fusing the spleen cells with a myeloma cell line, and permitting such fusion cells to form a hybridoma cell which secretes monoclonal antibodies capable of binding either the ICAM-1 antigen or the CD18 antigen, respectively.

The hybridoma cells, obtained in the manner described above, may be screened by a variety of methods to identify desired hybridoma cells that secrete antibody capable of binding to ICAM-1 antigen or CD18 antigen. In a preferred screening assay, such molecules are identified by their ability to inhibit the aggregation of Epstein-Barr virus-transformed cells. Antibodies capable of inhibiting such aggregation are then further screened to determine whether they inhibit such aggregation by binding to ICAM-1 or CD18 glycoprotein complex antigen, respectively.

The ability of an antibody to bind to a cell, such as a endothelial or a neutrophil, may be detected by means commonly employed by those of ordinary skill. Such means include immunoassays, cellular agglutination, filter-binding studies, antibody precipitation, etc.

The antibodies of the present invention may be obtained by natural processes (such as, for example, by inducing an animal to produce a particular ICAM-1 polyclonal antibody or CD18 glycoprotein complex polyclonal antibody) or by hybridoma technology (such as, for example, to produce monoclonal antibodies capable of binding to ICAM-1 or CD18 antigen). The choice of which method to employ will depend upon factors such as convenience, desired yield, etc. It is not necessary to employ only one of the above described methods, processes, or technologies to produce an anti-aggregation agent. The above-described processes, methods, and technologies may be combined in order to obtain a particular anti-aggregation agent to inhibit aggregation of neutrophils either to each other or to endothelial cell surfaces.

The particular R 6.5 and R 15.7 antibodies described with the present invention are said to be "substantially free of natural contaminants" if preparations which contain them are substantially free of materials with which these products are normally and naturally found.

In providing a patient with antibodies, or fragments thereof, capable of binding to the cell antigens described herein, or when providing the antibodies or functional derivatives or fragments thereof, to a recipient patient, the dosage of administered agent will vary depending on such factors as the patient's age, weight, height, sex, general medical condition, previous medical history, etc. Factors relevant to the determination of particular doses and regimens of the antibodies to be administered to a human patient may be determined by one of ordinary skill in the medical arts according to the individual physiological considerations of the patient and standard pharmacological practices (see Remington's *Pharmaceutical Sciences* (1980)).

As used according to the method for inhibiting or preventing the progression of thermal injury related tissue necrosis, additional factors such as the extent of burn injury to the patient (body surface percentage burned), age of the burn victim, severity of the burn (first, second, third degree burn), location of burn (face, back, arms, hands, genitals, feet), duration of exposure to the burning agent and the causative agent of the burn (chemical scalding water, oil, electrical, extreme cold, or heated object (machinery)), are additional factors to be considered in determining the appropriate dose. Subsequent doses of the antibody may be desired or necessary, depending upon the response of the patient to the initial treatment.

It is contemplated that the particular anti-inflammatory agents of the present method may also be administered topically, for example, as a cream or ointment. Such topical preparations may be formulated as a topical treatment (cream, ointment, etc.) according to methods well known to those of skill in the art, particularly in accord with those methods and materials described in Remington's *Pharma-* ceutical Science (18th edition) (1990), which reference is specifically incorporated herein by reference for this purpose.

A composition is said to be "pharmacologically acceptable" if its administration can be tolerated by a recipient patient. An agent is said to be administered in a "therapeutically effective amount" if the amount administered is physiologically significant. An agent is physiologically significant if its presence results in a detectable change in the physiology of a recipient patient. Most specifically, a detectable change in the physiology of a recipient patient may be monitored, for example, through observation of a decrease in the rate and amount of tissue destruction observed in the tissue immediately surrounding a thermal injury, such as a burn sight, on an animal, or a decrease in the influx of inflammatory cells (neutrophils) to tissue areas surrounding an injury, or by an observed maintenance of blood flow at least equal to non-injured burn sites.

While the exact extent or percentage of tissue necrosis around a burn site is still under study, the tissue necrosis is believed to progress to surrounding tissues to about 20% to 40% of the skin surface area of the original thermal injury (burn) site within a 24-hour time period post-injury. Therefore, it is preferable to provide the animal with the herein-described treatments and methods as soon as possible after the thermal injury.

By employing the anti-inflammatory cell agents of the present invention, obstruction of microscopic blood vessels may be prevented, and result in a reduction in tissue destruction, scarring, long-term disability, and the required length of patient hospitalization. However, mechanical obstruction is only one factor in heat injury mediated progressive tissue necrosis. Functional activation with stimulation of neutrophils to release enzymes, free radicals, etc. are other, perhaps more important, contributors to progressive tissue necrosis which are also inhibited to reduce tissue necrosis and scarring at thermal-injury sites according to the present invention.

The antibodies of the present invention can be formulated according to known methods to prepare pharmaceutically useful composition, whereby these materials, or their functional derivatives, are combined in a mixture with a pharmaceutically acceptable carrier vehicle. Suitable vehicles and their formulation, are described for example in Remington's *Pharmaceutical Sciences* (16th ed., Osol, A., Ed., Mack, Easton, Pa. (1980))[22]. In order to form a pharmaceutically acceptable composition suitable for effective administration, such compositions will contain an effective amount of an antibody, or their function derivative, together with a suitable amount of carrier vehicle. Most preferably, the carrier vehicle is a Ringers solution or a Hanks solution.

Additional pharmaceutical methods may be employed to control the duration of action. Control release preparation may be achieved through the use of polymers to complex or absorb antibodies (either the anti-ICAM-1 antibody or the anti-CD18 antibody) or their functional derivatives. Another possible method to control the duration of action by controlled release preparation is to incorporate an anti-aggregation agent (i.e., either of the antibodies) or their functional derivatives into particles of a polymeric matrix such as polyesters, polyamino acids, hydrogels, poly(lactic acid), or ethylene vinyl acetate copolymers. Alternatively, instead of incorporating these agents into polymeric particles, it is possible to entrap these materials in microcapsules prepared, for example, by coascerbation techniques or by interfacial polymerization, for example, hydroxymethyl cellulose or gelatine microcapsules and poly (methylacelate) microcapsules, respectively, or in colloidal drug delivery systems, for example, liposomes, albumin microspheres, microemulsion, nano particles, and nano capsules, or in macroemulsions. Such techniques are disclosed in Remington's *Pharmaceutical Sciences* (1980). The preparations of the present methods may also be provided to a patient transdermally.

Animal Model

The New Zealand White rabbit (1.5–2.0 kg) was the in vivo model employed to examine inflammation and thermal injury necrosis in the present studies. These animals are the smallest animals thus far identified in which the monoclonal antibodies directed against the CD18 complex and the ICAM-1 molecule of humans cross react. The following procedures were followed in the studies described herein. Animals were anesthetized by Isoflurane® inhalation.

Laser Doppler Blood Flowmetry:

The laser doppler blood flow probe connected to a blood flow meter (PF3, Perimed) was positioned on the space between the burned sites allowing consistent placement of the probe at different time points along with several areas of measurement at each time point.

Radio-labeling of Rabbit Neutrophils:

PMN's were isolated following the methods of Boykin[5]. Blood samples were anticoagulated with $ACD_i(4:1)$ and combined with dextran (mol wt 100,000–200,000) and PBS resulting in a separation of WBC rich plasma from RBC's in 30–40 minutes, the WBC rich plasma was then washed, re-suspended and subjected to hypotonic lysis and again washed and re-suspended. The PMN population was sedimented from the mononuclear cells using Ficoll-hypaque centrifugation at 475 G and yielded a PMN population of >95% with (97–99% viability by trypan blue dye exclusion). PMN's were then re-suspended $5 \times 10^6$ and radiolabeled with $^{51}C4$ (150 $\mu Cl/2 \times 10^7$PMN's).

Histology

Animals to be used for histology were euthanized and the abdominal aorta rapidly cannulated and flushed of blood by instillation of saline and then perfused with glutaraldehyde to fix the tissues for light and electron microscopy.

Monoclonal Antibodies

R 15.7 is a murine derived monoclonal antibody initially generated against the CD18 complex of canine neutrophils. The antibody cross reacts with both human and rabbit neutrophils. This monoclonal antibody was provided by R. Rothlien, PhD, at Boehringer Ingelheim Pharmaceuticals, Inc. R 15.7 was administered as described in the present studies by intravenous injection at a dose of 1.0 mg/kg.

R 6.5 is a murine derived monoclonal antibody directed against the endothelial ligand for PMN adherence, ICAM-1. It was administered in a dose of 2.0 mg/kg. Saline was the vehicle for mAb solution and was also used as a control solution. Analgesic methods employed in the present study included an intravenous injection of buprenorphine (0.05 mg/kg) every 12 hours for the duration of the study. Animals were sacrificed by the intravenous injection of pentobarbital (120 mg/kg).

Analysis of Data:

Burn size, blood flow, leukocyte counts and $^{51}Cr$ accumulation were compared between groups using analysis of variance (ANOVA) and Mann-Whitney U-test to provide the analysis of the date.

PMNs were isolated and radiolabeled with $^{51}Cr$ then reinjected prior to burn injury. Animals were burned as outlined herein with a brass probe. The animals were then biopsied at 6, 12, 24, 48 and 72 hours post burn and biopsies obtained at multiple sites. The biopsy samples were then assayed for $^{51}$Cr accumulation. An increase in the amount of $^{51}$Cr over the time period examined would be demonstrated if PMN's were the mediators of the injury, while the blood flow in the marginal zone of stasis would decrease.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

Preparation of Monoclonal Antibodies to Neutrophil Antigen CD18

The present example is provided to demonstrate one preferred method for preparing the monoclonal antibody specific for CD18 glycoprotein complex antigen of polymorphonuclear neutrophils. The present example is submitted also to satisfy best mode requirements for preparing the anti-CD18 monoclonal antibody of the present invention.

R 15.7 is a monoclonal antibody specific for the CD18 glycoprotein complex antigen. This monoclonal antibody is shown by the present inventors to block adherence and aggregation of polymorphonuclear neutrophils to each other. Also, the monoclonal antibody provides a method for treating and inhibiting the progression of tissue necrosis surrounding thermally injured tissues by preserving the integrity of the microvasculature surrounding an injured tissue area.

Immunization for R 15.7 Identification

Balb/CJ mice were immunized i.p. against glycogen elicited peritoneal macrophages from dogs on days -60 ($6 \times 10^6$ cells), -45 ($8 \times 10^4$ cells), -4 ($2 \times 10^7$ cells) and -3 ($2 \times 10^7$ cells) prior to fusion. This generated an antibody that cross-reacted with rabbits which was important for this study only. Other antibodies to CD18 may be generated by immunizing an animal with human cells.

Fusion

Fusions were carried out and resultant hybridoma supernatants were screened for inhibition of JY cell homotypic aggregation.

Selection for Anti-CD18 Positive Cells

Hybridomas producing desired supernatants with monoclonal antibody were cloned by limiting dilution 3 times, and the resultant hybridoma R 15.7.B8.C7.B1.H4 was selected. R 15.7.B8.C7.B1.H4 was determined to be an IgG1 isotype as determined by both ouchterlony (Mouse Monoclonal Typing Kit, ICM #64-6901; lot #mmtk25; plate #mo325) and ELISA (Zymed #90-6550, lot #71000071).

Specificity of R 15.7.B8.C7.B1.H4 was confirmed in FACS by showing that R 15.7.B8.C7.B1.H4 bound to mouse/human hybrids expressing human beta subunits of LFA-1 with mouse alpha subunits but not binding to hybrids expressing human alpha subunits with mouse beta subunits.

Monoclonal antibodies specific for CD18 glycoprotein are stored frozen at 0° C. until ready for use. The monoclonal antibodies were stable to freezing, and there was virtually no loss (<5% loss) of bioactivity after freezing for years with no loss of activity stored frozen. The hybridoma cell line producing R 15.7 is stored in the inventors laboratory at the following address:

Peter Lipsky, M.D.
Internal Medicine/Rheumatology
University of Texas Southwestern Medical School
5323 Harry Hines Blvd.
Dallas, Tex. 75235-9031

EXAMPLE 2

Preparation of Monoclonal Antibodies to Endothelial Cell ICAM-1

R 6.5 is an antibody to the endothelial ICAM-1 complex. This monoclonal antibody has been shown by the present inventors to prevent neutrophil-mediated microvascular injury and the progression of tissue necrosis to tissues surrounding a thermally compromised tissue site. Monoclonal antibodies were prepared substantially as described in EP 0314863A2.[18] The hybridoma which produces this antibody has been deposited with the ATCC (HB 9580). The protocol employed for preparing the monoclonal antibody R 6.5 is as follows.

Immunization

A Balb/C mouse was immunized intraperitoneally (i.p.) with 0.5 mls of $2 \times 10^7$ JY cells in RPMI medium 103 days and 24 days prior to fusion. On day 4 and 3 prior to fusion, mice were immunized i.p. with $10^7$ cells of PMA differentiated U937 cells in 0.5 ml of RPMI medium.

Differentiation of U937 Cells

U937 cells (ATCC CRL-1593) were differentiated by incubating them at $5 \times 10^5$/ml in RPMI with 10% Fetal Bovine Serum, 1% glutamine and 50 $\mu$g/ml gentamicin (complete medium) containing 2 ng/ml phorbol-12-myristate acetate (PMA) in a sterile polypropylene container. On the third day of this incubation, one-half of the volume of medium was withdrawn and replaced with fresh complete medium containing PMA. On day 4, cells were removed, washed and prepared for immunization.

Fusion

Spleen cells from mice immunized were fused with $P3 \times 63_{23}$ Ag8-653 myeloma cells at a 4:1 ratio according to Galfre et al. After the fusion, cells were plated in a 96 well flat bottomed microtiter plates at $10^5$ spleen cells/well.

Selection for Anti-ICAM-1 Positive Cells

After one week, 50 $\mu$l of supernatant were screened using a qualitative aggregation assay with both JY and SKW-3 as aggregating cell lines. Cells from supernatants inhibiting JY cell aggregation but not SKW-3 were selected and cloned two times utilizing limiting duration.

This procedure resulted in the identification and cloning of three separate hybridoma lines which produced anti-ICAM-1 monoclonal antibodies. The antibodies produced by these hybridoma lines were $IgG_{2a}$, $IgG_{2b}$, and IgM, respectively. The hybridoma cell line which produced the $IgG_{2a}$ anti-ICAM-1 antibody was given the designation R6.5.D6.E9.B2. The antibody produced by the preferred hybridoma cell line was designated R6.5.D6.E9.B2 (herein referred to as R 6.5-D6). Hybridoma cell line R6.5.D6.E9.B2 was deposited with the American Type Culture Collection, 10801 University Boulevard, Manassas, Va. 20110-2209 on Oct. 30, 1987 and given the designation ATCC HB 9580.

EXAMPLE 3

Treatment of Neutrophil-mediated Inflammation

The present example provides a method for inhibiting inflammation in an animal. More specifically, the present example establishes the utility of the present invention using a monoclonal antibody directed against CD18 antigen for treating and reducing neutrophil-mediated inflammation in an animal. The therapeutic agent employed in the present example is a monoclonal antibody which recognizes a functional epitope on CD18, designated R 15.7. The preparation of this monoclonal antibody is described at Example 1.

Patients who suffer from a disease known as "leukocyte adherence deficiency disease" ("LAD"[21]) have been observed to be unable to express leukocyte adhesion molecules on the surfaces of their cells. These patients have also been observed to be unable to mount a normal inflammatory response, supposedly because of the inability of their granulocytes to attach to cellular substrates. Granulocytes from LAD patients are also unable to get to sites of inflammation, such as at skin infections, due to their inability to attach to the endothelial cells in the blood vessel near the inflammation lesions. By rendering the polymorphonuclear cells incapable of adhering to cellular substrates, leukocyte mediated inflammatory response may be prevented. According to the present method, polymorphonuclear neutrophil mediated inflammation, particularly that attendant thermal injury, may be prevented and/or inhibited through treatment with an anti-CD18 monoclonal antibody.

The anti-CD18 monoclonal antibody may be prepared as outlined in Example 1. For use in the inhibition and/or prevention of polymorphonuclear neutrophil mediated inflammation, the monoclonal antibody may be administered to a patient, most preferably by intravenous administration, at a dose of between 1 mg/kg to 10 mg/kg. Most preferably, the dose of anti-CD18 monoclonal antibody should be between about 1 mg/kg to about 5 mg/kg. Treatment with the monoclonal antibody may be repeated dependent upon patient response after initial antibody treatment.

Most preferably, the anti-CD18 monoclonal antibody should be prepared in a pharmaceutically acceptable carrier solution. By way of example, such a pharmaceutically acceptable carrier solution may be sterile saline.

EXAMPLE 4

In Vivo Treatment of Thermal Injury With Anti-ICAM or Anti-CD18 Monoclonal Antibodies The present example is provided to demonstrate the utility of the present method for treating and preventing necrosis or tissue death surrounding a tissue burn site in vivo. The results demonstrate that administration of an antibody specific for neutrophil CD18 antigen or an antibody specific for endothelial cell ICAM-1 antigen to an animal prior to a thermal injury will reduce the extent of tissue necrosis surrounding a thermal injury contact site, compared to non-pretreated animals. The present example also demonstrates the utility of the claimed invention as post-thermal injury treatment, as treatment with the described antibodies within three hours of a thermal injury will reduce the extent of tissue necrosis surrounding thermal injury, compared to animals not treated with the antibody.

A model for examining thermal injury and tissue necrosis was developed using New Zealand White rabbits. Under general anesthesia, 2 sets of 3 full thickness burns separated by two 5×30 mm zones were produced by applying brass probes heated to 100° C. to the animals' backs for 30 seconds. The full thickness burns produce tissue damage characteristic of third degree burns in humans. The burned contact site regions on each animal represented <5% total percent body surface area burn, and did not result in any detectable changes in behavior or feeding, or significant changes in cutaneous blood flow at shaved unburned skin sites, in any of the groups tested.

Cutaneous blood flow determinations were obtained for 72 hours in each group of animals. Blood flow measurements were performed using a laser doppler blood flowmeter (PF3, Perimed. Piscataway, N.J.). Five (5) study groups were examined:

1. Controls given saline alone (n=12);
2. Animals given R 15.7 monoclonal antibody prior to burn injury (pre-R 15.7, n=5);
3. Animals given R 15.7 monoclonal antibody 30 minutes after burn injury (post-R 15.7, n=6);
4. Animals given the anti-ICAM-1 antibody, R 6.5 prior to burn (pre R 6.5, n=6); and
5. Animals given the R 6.5 monoclonal antibody 30 minutes post-burn injury (post-R 6.5, n=6).

Methods

The New Zealand white rabbits (1.0–1.5 kg) were anesthetized and then the animals' backs were shaved and venous access was obtained by cannulation of a peripheral ear vein with an angiocath (24 gauge). Catheter patency was maintained by twice daily flushes with 1.0 ml of heparin (10 U/ml). Blood samples were obtained by venipuncture of a peripheral ear vein. Leukocyte (WBC) counts were performed using a hemocytometer. Hematocrit (Hct) was determined with capillary microcentrifugation. Cutaneous blood flow (BF) measurement was performed using a laser doppler blood flow meter (Periflux-PF3, Perimed Inc., Piscataway, N.J.) and an integrating flow probe (PF 313, Perimed Inc., Piscataway, N.J.) containing 7 efferent laser fibers and 14 afferent fibers which reflect capillary perfusion in a tissue volume of approximately 1200 mm$^3$ (Perimed Inc., Piscataway, N.J.).

Previous studies have shown good correlation between laser doppler blood flow measurement and standard radio-labeled microsphere calculations of blood flow.[17]

Leukocyte (WBC) counts and hematocrits (Hct) were obtained at baseline, immediately post burn, at 24, 48 and 72 hours post burn. Under general anesthesia (isoforane), 2 sets of 3 full thickness burns separated by two 5×30 mm zones were produced by applying brass probes heated to 100° C. to the animals' backs for 30 seconds (FIG. 1). Production of full thickness burns in this manner allowed for the measurement of the lateral extension of the burn into the "zone of stasis" between injury sites.

Baseline blood flow was measured at designated burned sites, marginal zones, and shaved unburned skin sites and repeated 1, 2, 3, 4, 24, 48 and 72 hours post burn.

The murine derived antibodies, R 15.7 and R 6.5, were produced and purified as previously described in Example 1 and Example 2, respectively, and administered in sterile saline. Both the R 15.7 and R 6.5 were given in a single dose by intravenous injection. The dose of R 15.7 was 1.0 mg/kg and the dose of R 6.5 was 2.0 mg/kg. These doses were selected based on previously reported efficacy in the studies cited above. All animals were given analgesic (buprenorphine 0.05 mg/kg IV) every 12 hours throughout the study period.

Two animals in each group were anesthetized and biopsies of one burn site obtained at 24 hours post-burn, for histologic comparison of burn depth, edema, and leukocyte infiltration. Animals were evaluated twice daily for pain and suffering by using a quantitative pain scale and were euthanized if pain or suffering were severe. At 72 hours post-burn, the zones between the burn sites were evaluated for gross evidence of progression, and the number of zones with complete progression to confluent necrosis between burn sites tabulated. Animals were euthanized at the conclusion of the 4-day study with a lethal intravenous injection of pentobarbital (150 mg/kg). Statistical analysis of the data was performed with One-way Analysis of Variance and the Mann-Whitney U test. Significance was assigned to p<0.05. Values in text are given as mean±SD, figures represent mean±SEM.

Results

Base Line Weight, Hematocrit, Leukocyte Counts

There was no significant difference in baseline weight, hematocrit or leukocyte counts among the five groups. One animal in the pre-R 6.5 group was euthanized 24 hours post-burn. Hematocrit remained unchanged in each group throughout the length of the study.

Elevation in leukocyte counts were observed at 24 hrs in the pre-R 15.7 (18,000±8.300 cells/mm$^3$), the post-R 15.7 groups (37.800±8.300 cells/mm$^3$) in the pre-R 6.5 (18, 300±4.900 cells/mm$^3$), and the post-R 6.5 (24.100±6.100 cells/mm$^3$) groups, compared to controls (8,500±2,300 cells/mm$^3$). White blood cell counts in both of the antibody treated groups returned to the levels of the control animals by 48–72 hours post-burn.

The polymorphonuclear leukocytosis observed in the R 15.7 and the R 6.5 groups at 24 hours post-burn has been observed in other animal models (unpublished personal observation). Such may represent the release into the circulation of a marginated pool of polymorphonuclear leukocytes.

Blood Flow

Figure 2:
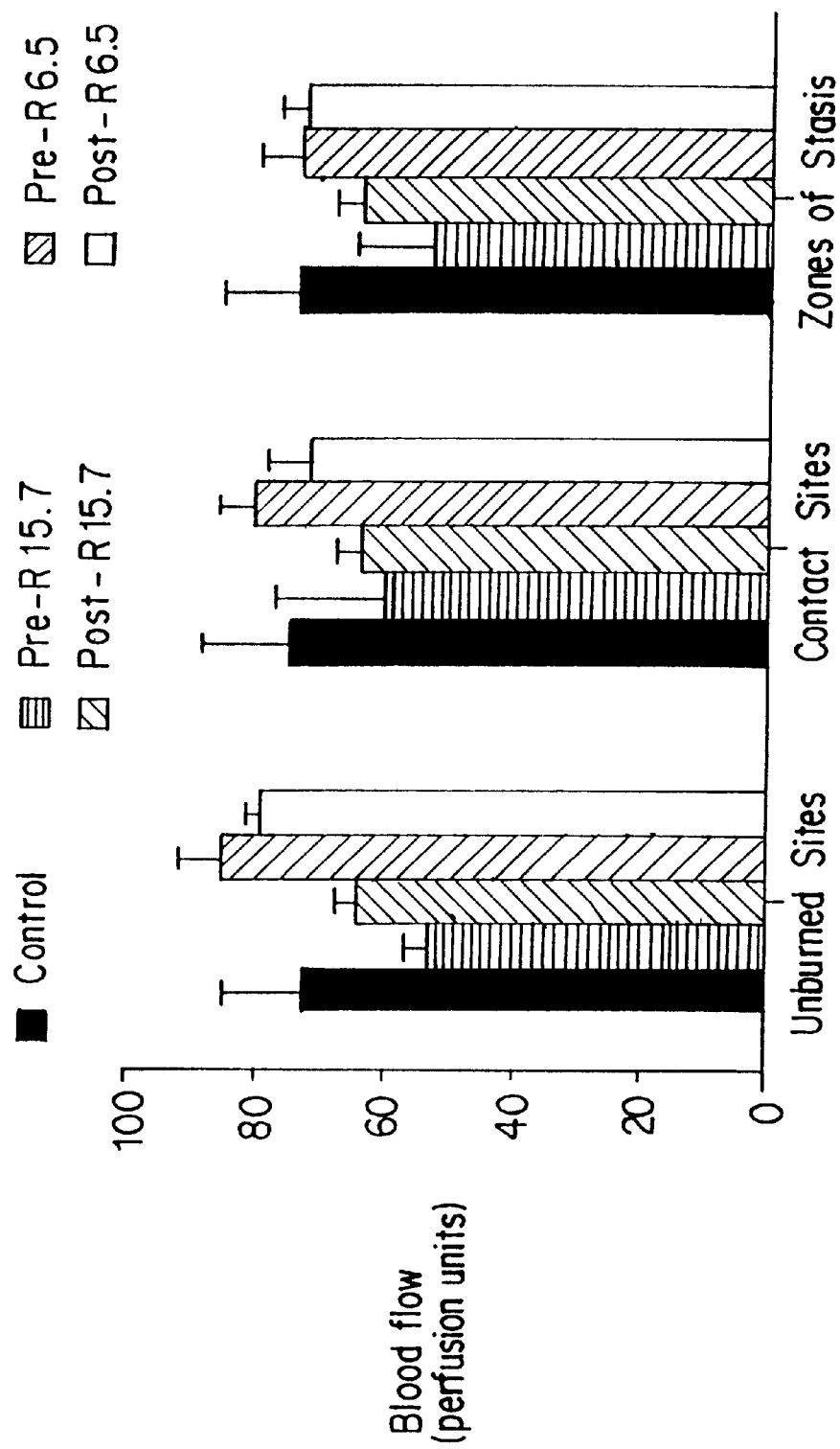
FIG. 2—New Zealand white rabbits as animal models Baseline cutaneous blood flow as determined with laser doppler blood flowmeter for Controls (n=12). Animals given monoclonal antibody R 15.7 prior to burn injury (pre-R 15.7, n=5), animals given R 15.7 30 minutes after burn injury (post-R 15.7, n=6), animals given monoclonal antibody R 6.5 prior to burn injury (pre-R 6.5, n=6), and animals given R 6.5 30 minutes after burn injury (post-R 6.5, n=6). Measurements presented are mean±SEM for each group in absolute perfusion units. There were no statistically significant difference between groups or from site to site within groups.

Baseline cutaneous blood flow in absolute perfusion units (PU) as measured with the laser doppler blood flow meter are presented (FIG. 2) for burn sites, the marginal zones, and the shaved unburned skin sites in each of the experimental groups. There were no significant differences in baseline cutaneous blood flow.

Shaved Unburned Skin Sites

Figure 3:
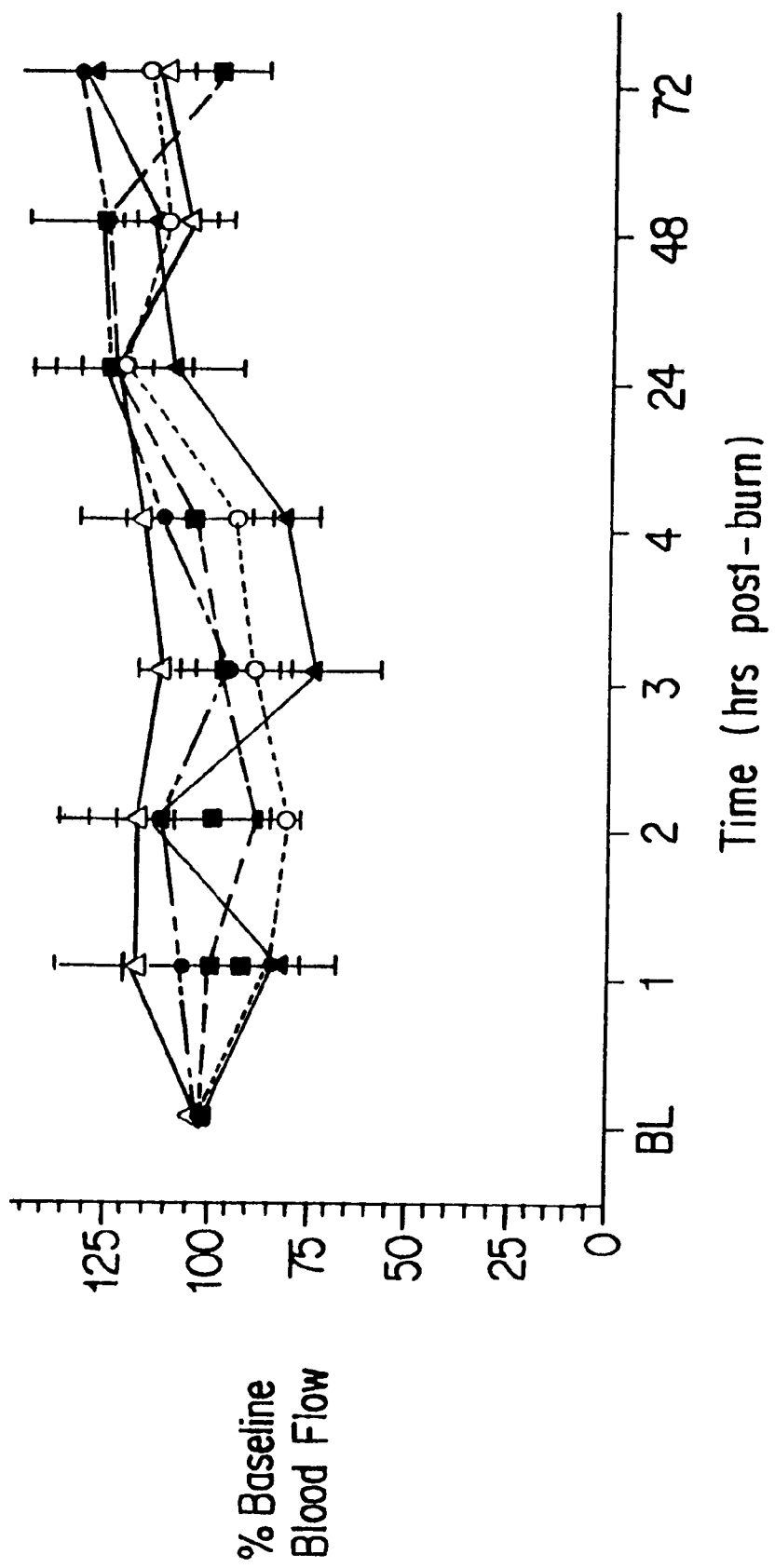
FIG. 3—New Zealand white rabbits were used as animal models Cutaneous blood flow at shaved but unburned skin sites determined by laser doppler blood flowmeter are presented as percent of baseline values for Controls (n=12), animals given monoclonal antibody R 15.7 (anti-CD18) prior to burn injury (pre-R 15.7 n=5), animals given R 15.7 30 minutes after burn injury (post-R 15.7, n=6), animals given monoclonal antibody R 6.5 (anti-ICAM-1) prior to burn injury (pre-R 6.5, n=6), and animals given R 6.5 30 minutes after burn injury (post-R 6.5, n=6). There was no significant difference between groups, blood flow at the shaved unburned sites remained essentially unchanged over the 72-hour period of observation.

Serial changes in blood flow in the shaved unburned skin sites, presented as a percent of baseline (FIG. 3), showed no statistically significant difference among groups at each evaluation point (1 hour, 2 hours, 3 hours, 4 hours, 24 hours, 48 hours and 72 hours).

Burn Contact Sites

Figure 4:
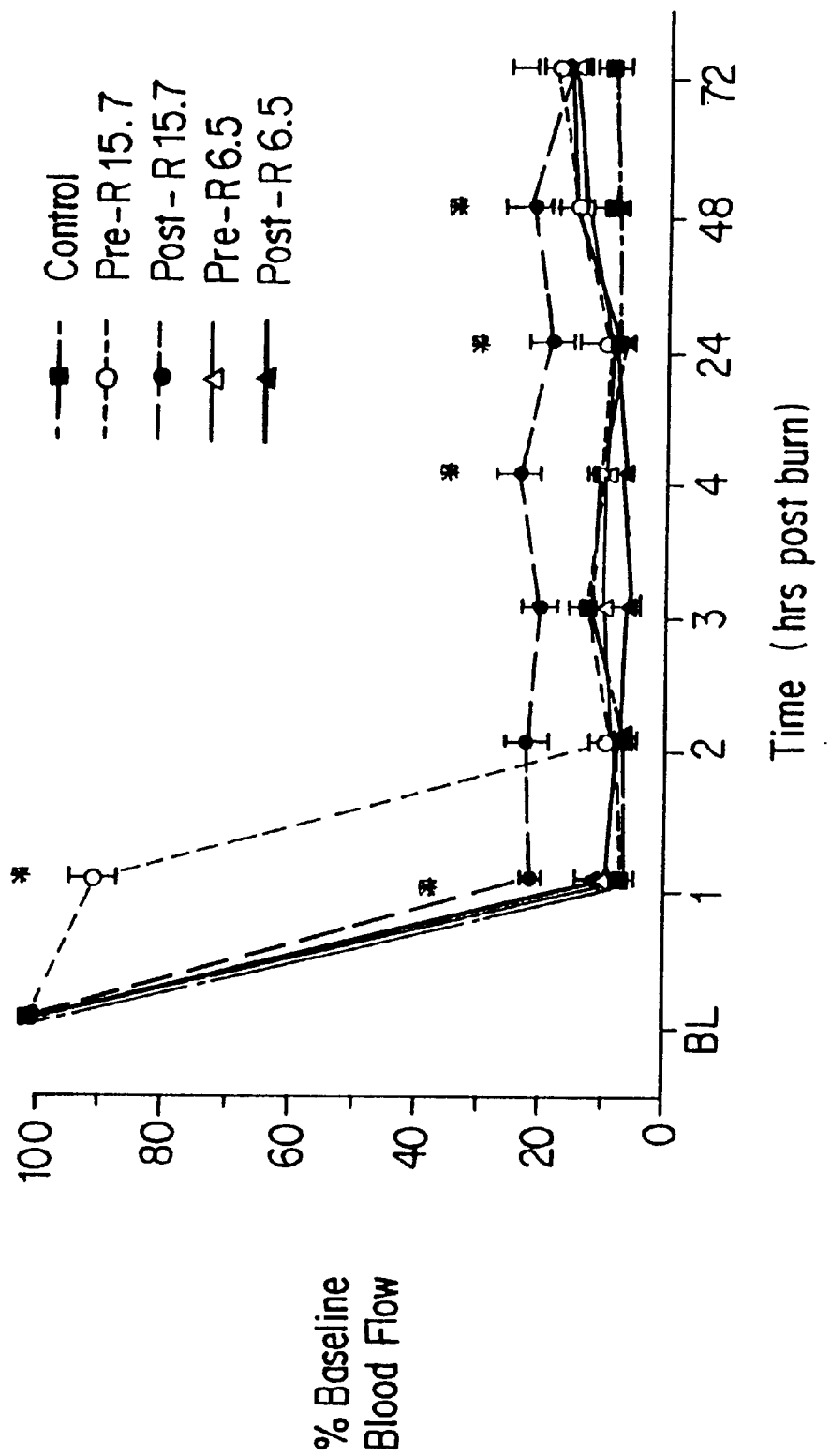
FIG. 4—New Zealand white rabbits were employed as animal models Cutaneous blood flow at heated probe burn contact sites (100° C.) determined by laser doppler blood flowmeter are presented as percent of baseline values for Controls (n=12), animals given monoclonal antibody R 15.7 prior to burn injury (pre-R 15.7 n=5), animals given R 15.7 30 minutes after burn injury (post-R 15.7, n=6), animals given monoclonal antibody R 6.5 prior to burn injury (pre-R 6.5, n=6), and animals given R 6.5 30 minutes after burn injury (post-R 6.5, n=6). There was a significant and persistent reduction in relative blood flow observed in all groups, however the post R 15.7 animals maintained levels relatively higher compared to baseline than any of the other experimental groups. "*" indicates p<0.05.

Blood flow in burn contact sites expressed as a percent of baseline are shown in FIG. 4. All groups demonstrated immediate and persistent decreases in perfusion to less than 20% of baseline blood flow, which persisted through day 3 post-burn. The consistent reduction in blood flow at the burn sites observed among all groups indicates the equivalents of the burn injury produced in each set of animals.

Zones of Stasis

Figure 5:
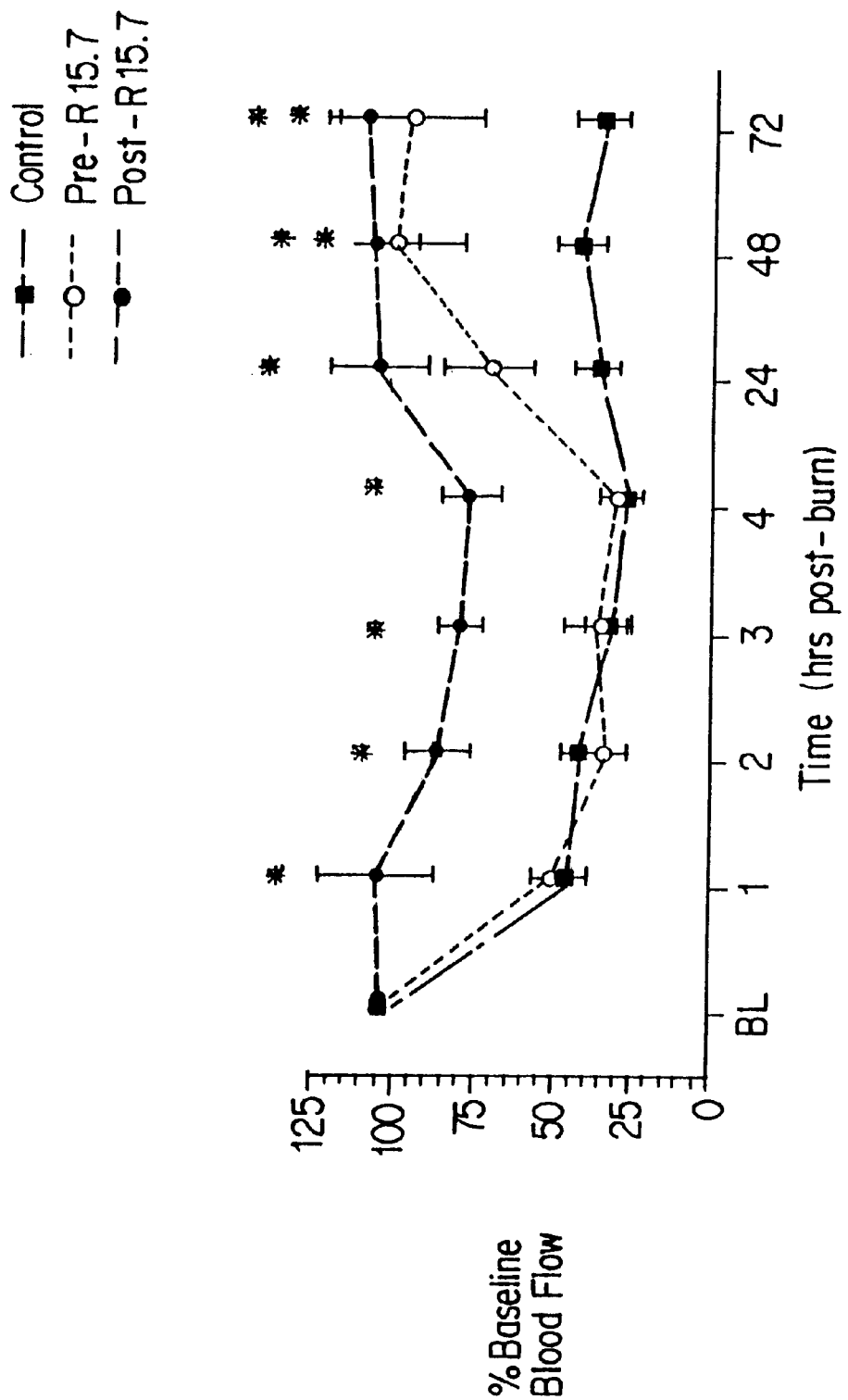
FIG. 5—New Zealand white rabbits were employed as animal models Relative changes in cutaneous blood flow in the zones of stasis determined by laser doppler blood flowmeter are presented as percent of baseline values (mean±SEM) for Controls (n=12), animals given monoclonal antibody R 15.7 prior to burn injury (pre R 15.7, n=5), and animals given R 15.7 30 minutes after burn injury (post-R 15.7, n=6). "*" indicates p<0.05.

Serial blood flow measurements in the marginal zones of stasis for controls and the pre and post administration of anti-CD18 antibody, R 15.7, are shown in FIG. 5. The control animals developed decreases in blood flow in the initial post-burn period which persisted throughout the 72-hour period of observation. The pre-R 15.7 group also developed decreases in perfusion in the zone of stasis initially, but showed gradual recovery over 24, 48 and 72 hours, which were significantly (P<0.05) higher than the blood flow seen in the control group.

The post-R 15.7 group showed even greater improvements in blood flow over the course of the study, with values significantly higher than controls at all time points. Both the pre-R 15.7 and post-R 15.7 groups had perfusion near baseline at the conclusion of the 72-hour observation period.

Figure 6:
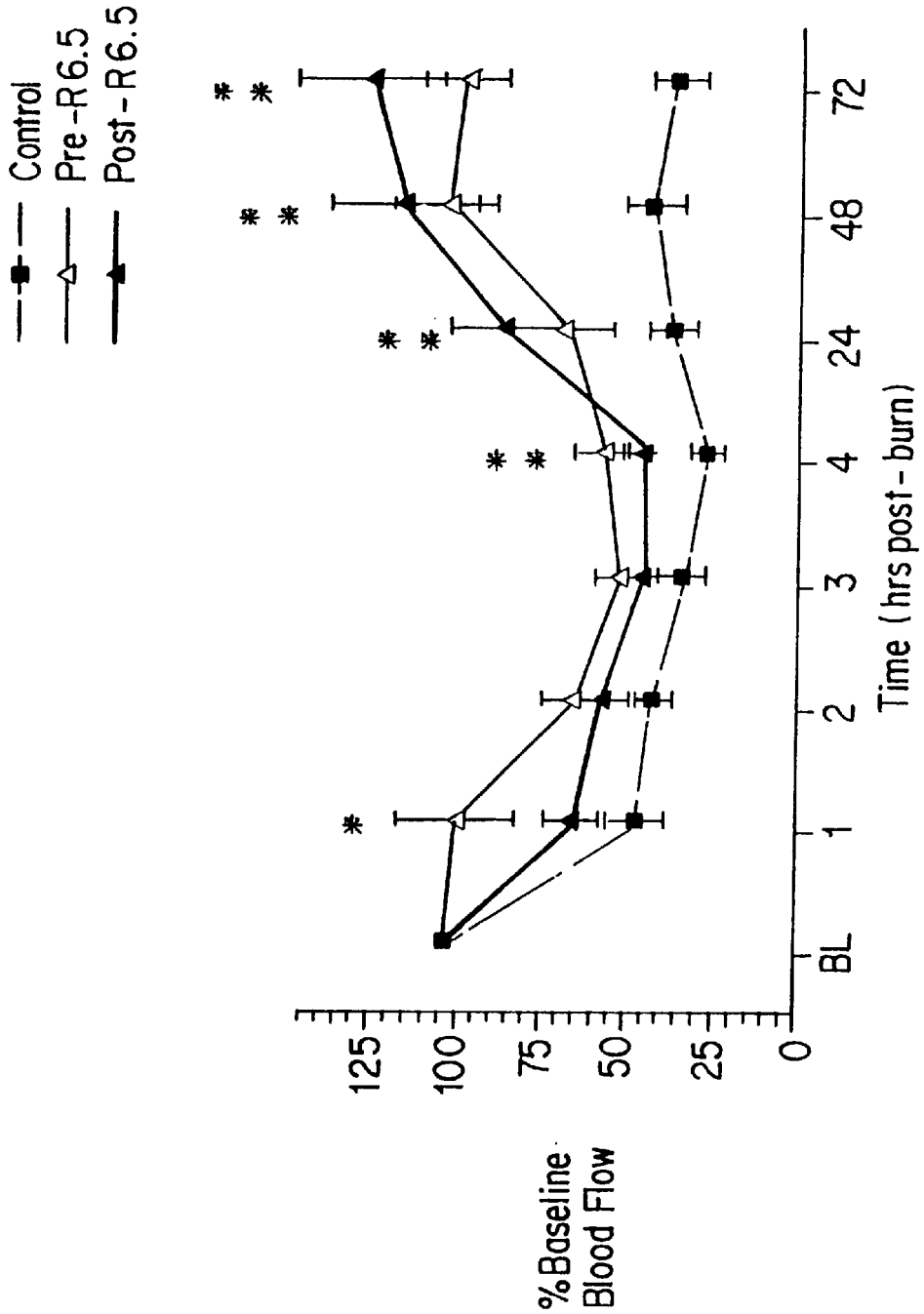
FIG. 6—New Zealand white rabbits were employed as animal models Relative changes in cutaneous blood flow in the zones of stasis determined by laser doppler blood flowmeter are presented as percent of baseline values (mean±SEM) for Controls (n=12), animals given monoclonal antibody R 6.5 prior to burn injury (pre-R 6.5, n=6), and animals given R 6.5 30 minutes after burn injury.

The serial blood flow measurements in the marginal zones of stasis for the pre-R 6.5 and the post-R 6.5 groups are presented in FIG. 6, along with the controls again presented for comparison. The pre-R 6.5 monoclonal antibody group had relative blood flow values significantly greater than controls at 1, 4, 24, 48 and 72 hours post-burn. The post-R 6.5 monoclonal antibody group had relative blood flow values significantly above control at 4, 24, 48 and 72 hours. Just as in the R 15.7 groups, both the R 6.5 groups had relative blood flow values near or above baseline levels at 72 hours.

Burn Site Histology

On gross histologic examination of the burn contact sites of all five groups were clearly full thickness injuries, corresponding to that injury characteristic of a third degree burn in humans.

The visual evidence of burn extension in the marginal zones of ischemia to the point of confluence with the probe contact sites was observed in 18 of 44 zones in the control animals (40.9%), 5 of 20 (25%) zones in the pre-R 15.7 group, 1 of 20 (5%) zones in the post-R 15.7 group, 1 of 15 (6%) zones in the pre-R 6.5 and 1 of 20 (5%) zones in the post-R 6.5 group. Histologic evaluation of marginal zones in control animals showed edema, infiltration with inflammatory cells, necrosis of epidermis and dermal appendages, vascular occlusion and inflammation of subdermal muscle, whereas animals receiving either R 15.7 or R 6.5 developed only edema of the dermis. There was no evidence of infection in any of the groups.

control=40.9% pre-R 15.7=25%

Post-R 15.7=5%

Pre-R 6.5=6% post-R 6.5=5%

The results indicate an improvement in microvascular perfusion from treatment with the described antibodies. The data indicate that progressive tissue ischemia in the surrounding zone of stasis (tissue immediately surrounding the burn contact site) is attenuated by treatment of the animal with the described monoclonal antibody, R 15.7 or R 6.5. Inhibition of inflammatory cell adherence with the anti-CD18 antibody, R 15.7, and the anti-ICAM-1 antibody, R 6.5, prior to and 30 minutes following burn injury is demonstrated to improve microvascular perfusion in the marginal zone of stasis following thermal injury in vivo. The results support the role of inflammatory cells as central mediators of the microvascular injury responsible for extension of burn size in the "zone of stasis" (tissue surrounding a burn site), and demonstrates the utility of the present invention for inhibiting and preventing tissue necrosis attendant upon thermal injury in vivo.

EXAMPLE 6

Proposed Treatment of Human Thermal Injury

The present example is provided to demonstrate the utility of the claimed method for the treatment of human thermal injuries, particularly burns, characterized as first degree, second degree, and third degree burns. The present methods are contemplated to provide inhibition of tissue necrosis at a burn site which extends both laterally and horizontally (into the depths of the tissue) of a burn site.

First degree burns are characterized by pain and redness, and typically the outer layer of injured cells will peel away within a few days of the burn, and leaving a totally healed subadjacent skin with no residual scarring. A second degree burn is characterized as either a superficial (with attendant blister formation) or a deep, partial thickness burn (more akin to a full thickness or third degree burn). With the partial thickness second degree burn, the survival of the uninjured dermis and the associated epidermal appendages is at risk unless optimal conditions for preservation of these elements can be maintained. A third degree burn is characterized by a full thickness destruction of the dermis, and an attendant incapability of the dermis to heal spontaneously.

The treatment of burns provided by the present invention may effect a prevention and/or inhibition of tissue necrosis in areas surrounding a primary burn contact site. The present example, along with the protocols outlined herein in the preparation of the therapeutic agents, provides one of ordinary skill in the medical arts, specifically in the clinical management of burn injuries, sufficient guidance for calculating specific dose levels for use in burn therapy which would be effective for preventing and/or inhibiting progressive tissue necrosis in areas surrounding an initial burn site in a human.

Monoclonal antibodies will be prepared as described herein at Example 1 (anti-CD18 monoclonal antibody) and Example 2 (anti-ICAM-1 monoclonal antibody). In a most preferred aspect of the invention, the purified preparations of monoclonal antibody are to be administered in sterile saline at a concentration of about 1.0 mg/kg for the anti-CD18 monoclonal antibody, and at a dose of about 2.0 mg/kg of the anti-ICAM-l monoclonal antibody. Where the two monoclonal antibodies are delivered in conjunction, the cumulative dose of anti-CD18 and ICAM-1 antibody should be between about 1.0 mg/kg and 2 mg/kg.

The described doses will be provided to the burn victim once a day. The size of the necrotic area surrounding a burn site will be monitored daily to assess the progress of tissue necrosis in tissue areas surrounding a burn contact site. No increase or an increase of less than 50% in the size of the area of tissue necrosis surrounding an initial burn contact site upon commencement of the human burn patient on a therapeutic regimen of the monoclonal antibodies herein described will provide an indication that the therapy is providing a pharmacologically effective treatment for the purposes defined herein (halting of tissue necrosis attendant thermal injury).

An observation that the area of surrounding tissue necrosis has been contained (no progression or less than 50% increase in the diameter of tissue necrosis in the area surrounding an initial burn contact site) will also provide an indication that the therapy has prevented or at least contributed to the inhibition of microvasculature compromise at the periphery of the necrotic tissue surrounding a burn contact site.

In this regard, the proposed method is expected to prevent, as well as inhibit, the progression of thermal-related tissue necrosis in burns contained to 80% or less body surface area, and which are not associated with serious underlying physiological system compromise (i.e., pulmonary involvement, sensory organ involvement (eyes, tongue), digestion system). Thermal injury the result of heat, cold, chemical, or electrical exposure may be effectively treated by administering to the patient a pharmacologically effective dose of a monoclonal antibody specific for ICAM-1 or CD18 antigen, or a treatment which includes a combination of the monoclonal antibodies. Most preferably, a monoclonal antibody specific for CD18 antigen or ICAM-1 antigen or a mixture thereof, is to be employed in the prescribed burn therapy method.

The vehicle employed for administering the monoclonal antibody CD18 or the monoclonal antibody ICAM-1 most preferred is a Ringers solution or Hanks solution (sterile). Optimally, the monoclonal antibody will be administered to a patient within three hours of thermal injury. However, the regimen is expected to therapeutically benefit the burn patient in the aspects already discussed when administered within six hours of burn injury.

Proposed Treatment Regimen for Thermal Injury Related Inflammation in an Adult Human Male The inflammation attendant upon thermal injury in an adult human male weighing on the average of 70 kg may be treated according to the following protocol. Initially, the patient should be evaluated to determine the type and extent of the thermal injury prior to use of the present method (tissue destruction corresponding to a first degree, second degree or third degree burn) (percent body surface area thermally injured according to techniques well known to those of skill in the art-1 palm surface equals about 1% body surface). The percentage of body surface area found to be involved in the burn injury should be less than 80% body surface area, and no serious compromise of the pulmonary, nervous and digestive systems should exist. The exact size of the thermally compromised (burn) contact sites (areas of tissue destruction) should be measured and recorded.

A dose of between 1 mg/kg and 10 mg/kg should then be administered to the patient (a dose of between 70 mg and 700 mg for a 70 kg adult), most preferably within the three hours after thermal injury. While the antibody may be administered by any variety of methods, the mode of administration most preferred is through intravenous administration, and the most preferred dose of the monoclonal antibody R 15.7, or R 6.5 is of between 70 mg and 350 mg in a single bolus treatment.

The size of the extent of tissue destruction should be measured surrounding each site of direct thermal injury at periodic intervals of one hour after initial administration of the antibody to assess patient response to the treatment. An effective therapy for treating inflammation will be determined where visual evidence of burn extension in the marginal zones of ischemia is less than 50% the size of the initial thermal injury contact site after 24 hours of the initial treatment. For example, where a skin burn area (3rd degree burn) encompasses a 10 cm$^2$ skin area, an effective therapy will be evidenced where the wound extension if less than 15.0 cm.$^2$ An additional dose of the antibody may be administered to the patient where visual evidence of burn extension is 50% or more of the size of the original burn contact site diameter after 24 hours of injury. Assessment of the size of the tissue area involved in tissue necrosis should be evaluated after such subsequent antibody treatments to determine if the progression of tissue necrosis has been halted.

The following references are specifically incorporated herein in pertinent part for the purposes indicated.

BIBLIOGRAPHY

1. Harlan, J. M. (1987) *Seminar in Thrombosis and Hemostasis*: Vessel Wall, 13 (4):434–44.
2. Vedder, N. B. et al. (1988) *J. Clijn. Invest.* 81:939–944.
3. Movat et al. (1987) *Patho Immunopathol. Res.*, 6:153–176.
4. Weiss, S. J. (1989) *N. Engl. J. Med.*, 320:365–376.
5. Boykin et al. (1980) *Plastic and Reconstructive Surgery*, 66 (2):191–198.

6. Deitch et al. (1990) *J. Trama*, 30:259–268.
7. Solem et al. (1986) *Am. J. Pathology*, 125:563–70.
8. Price et al. (1987), *J. Immunol.*, 139:4174–4177.
9. Pohlman et al. (1986) *J. Immunol.*, 136:4548–4553.
10. Arfors et al. (1987) *Blood*, 69:338–340.
11. Barton et al. (1989) *J. Immunol.*, 143:1278–1282.
12. Winn et al. (1991, in press) In: *The Immune Consequences of Trauma, Shock and Sepsis, Mechanism and Therapeutic Approaches*, Springer-Verlag.
13. Sharar et al. (1991, in press) In: *The Immune Consequences of Trauma, Shock and Sepsis, Mechanism and Therapeutic Approaches*, Springer-Verlag.
14. Mileski et al. (1990) *Surgery*, 108:206–212.
15. Wegner et al. (1990) *Science*, 247:456–459.
16. Cosimi et al. (1990) *J. Immunol.*, 144:4604–8.
17. Johnson, J. M. (1990) In: *Laser-Doppler Blood Flowmetry*, Shephard A. P. and Oberg P. A. Kluwer, Academic Publishers, Norwell, Mass., pp 121–39.
18. E.P. 0 314 863 A2—Anderson (filed Apr. 29, 1988)
19. Schmidt-Schonbein, G. W. (1987) *Fed. Proc.*, 46:2397–2401.
20. Anderson et al., (1988) *J. Clin. Investigation*, 82:1746
21. Galfre et al. (1977) *Nature*, 266:550.
22. Remington's *Pharmaceutical Sciences* (1980) 16th ed., Osol., A., Ed., Mack, Easton, Pa.
23. U.S. Pat. No. 4,965,271—Mandell et al. (1987).
24. Dustin, M. L. et al. (1986) *J. Immunol.*, 137:245.

What is claimed is:

1. A method for inhibiting skin tissue necrosis attendant a thermal injury in an animal comprising treating the animal with a therapeutically effective amount of an antibody that specifically binds an ICAM-1 antigen, thereby inhibiting ICAM-1 binding and inflammatory functions, in a pharmacologically acceptable carrier solution.

2. The method of claim 1 wherein the antibody is a monoclonal antibody.

3. The method of claim 1 wherein an antibody that binds to an ICAM-1 antigen is produced by ATCC #HB9580.

4. The method of claim 3 wherein the therapeutically effective amount of the monoclonal antibody is between 1 mg/kg to about 10 mg/kg.

5. The method of claim 3 wherein the therapeutically effective amount of the monoclonal antibody is between 2 mg/kg to about 5 mg/kg.

6. The method of claim 1 wherein the animal is a human or a rabbit.

7. The method of claim 1 wherein the thermal injury is a heat induced thermal injury.

8. The method of claim 7 wherein the heat induced thermal injury is an injury resulting from contact with heat of greater than 50° C.

9. The method of claim 1 wherein the pharmaceutically acceptable carrier solution is Ringers solution.

10. A method for inhibiting tissue necrosis in a tissue area surrounding a burn in an animal, the method comprising:
treating the animal with a therapeutically effective amount of an antibody that specifically binds to an antigen selected from the group consisting of an ICAM-1 antigen, a CD18 antigen, an L-selectin antigen, a CD44 antigen, a P-selectin antigen, an E-selectin antigen, and ICAM-2 antigen, thereby inhibiting the binding and inflammatory functions of ICAM-1, CD18, L-selectin, CD44, P-selectin, E-selectin or ICAM-2.

11. A method for inhibiting tissue necrosis at a thermal skin injury in an animal, the method comprising:
treating the animal with a therapeutically effective amount of an antibody that specifically binds to an antigen selected from the group consisting of ICAM-1 antigen, a CD18 antigen, an L-selectin antigen, a CD44 antigen, a P-selectin antigen, and an ICAM-2 antigen, thereby inhibiting the binding and inflammatory functions of ICAM-1, CD18, L-selectin, CD44, P-selectin, or ICAM-2.

12. The method of claim 10 or 11 wherein the antibody is capable of binding to an ICAM-1 antigen or a CD18 antigen.

13. The method of claim 12 wherein the antibody is a monoclonal antibody.

14. The method of claim 13 wherein the monoclonal antibody binds to an ICAM-1 antigen and is an antibody produced by a hybridoma ATCC #HB9580.

15. The method of claim 14 wherein the therapeutically effective amount of the monoclonal antibody is between 1 mg/kg to about 5 mg/kg.

16. The method of claim 13 wherein the therapeutically effective amount of the monoclonal antibody is between 1 mg/kg to about 10 mg/kg.

17. The method of claim 13 wherein the antibody is a monoclonal antibody capable of binding with a CD18 antigen.

18. The method of claim 1, 10 or 11 wherein the antibody is injected as a single bolus injection.

19. The method of claim 10 or 11 wherein the antibody is a monoclonal antibody and is administered intravenously as a single bolus at a dose of between 1 mg/kg to about 5 mg/kg.

20. The method of claim 11 wherein the thermal injury is a burn, cold, electrical or chemical injury.

21. The method of claim 11 wherein the thermal injury is a burn injury from exposure to temperatures greater than 50° C.

22. A method for inhibiting tissue necrosis at a heat injury site on an animal comprising:
treating the animal with a therapeutically effective amount of an antibody or an antigen binding fragment thereby, that specifically binds to an antigen selected from the group consisting of an ICAM-1 antigen, an L-selectin antigen, a CD44 antigen, a VLA-4 antigen, a P-selectin antigen, an E-selectin antigen, a CD18 antigen and an ICAM-2 antigen, thereby inhibiting the binding and inflammatory functions of ICAM-1, L-selectin, CD44, P-selectin, E-selectin, CD18, or ICAM-2.

23. The method of claim 22 wherein the antibody is capable of binding an ICAM-1 antigen, a CD18 antigen, or an antigen binding a fragment thereof.

24. The method of claim 23 wherein the antibody is a monoclonal antibody produced by a hybridoma ATCC #HB9580 or a polyclonal antibody.

25. The method of claim 23 wherein the monoclonal antibody is specific for an ICAM-1 antigen.

26. The method of claim 22 wherein the antibody is injected as a single bolus injection.

27. The method of claim 22 wherein the antibody is administered intravenously.

28. The method of claim 22 wherein the monoclonal antibody is administered intravenously as a single bolus at a dose of between 1 mg/kg to about 5 mg/kg.

29. A method for decreasing polymorphonuclear neutrophil mediated scarring in an animal having a second or third degree burn, said method comprising:
inhibiting polymorphonuclear neutrophil activity by treating an animal having a second or third degree burn with a therapeutically effective amount of a pharmaceutically acceptable preparation containing an antibody that binds to an antigen selected from the group consisting of CD18 antigen, an ICAM-1 antigen, an L-selectin antigen, a CD44 antigen, a P-selectin antigen, an E-selectin antigen and an ICAM-2 antigen, thereby inhibiting the binding and inflammatory functions of ICAM-1, L-selectin, CD44, P-selectin, E-selectin, CD18, or ICAM-2, to decrease polymorphonuclear neutrophil mediated tissue scarring in the animal.

30. The method of claim 29 wherein the animal is a human.

31. The method of claim 29 wherein the antibody is an anti-ICAM-1 antibody, an anti-ICAM-2 antibody, an anti-CD18 antibody, or a mixture thereof.

32. The method of claim 31 wherein the antibody is an anti-ICAM-1 antibody or an anti-CD18 antibody.

33. The method of claim 32 wherein the monoclonal antibody binds to an endothelial cell ICAM-1 antigen and is ATCC #HB9580.

34. The method of claim 31 wherein the antibody is a monoclonal antibody specific for CD18 antigen.

35. The method of claim 29 wherein the therapeutically effective amount is between about 1 mg/kg and about 10 mg/kg.

36. A method for inhibiting inflammatory cell-mediated and endothelial cell-mediated tissue necrosis at a skin burn site in an animal comprising treating the animal with a therapeutically effective amount of an antibody that inhibits tissue damage attendant a thermal injury capable of binding to an antigen selected from the group consisting of an ICAM-1 antigen, and anti-CD18 antigen or an antigen binding fragment thereof, thereby inhibiting the binding and inflammatory functions of ICAM-1 or CD18, in a pharmaceutically acceptable carrier solution.

37. The method of claim 36 wherein the inflammatory cell mediated tissue necrosis is polymorphonuclear neutrophil-mediated tissue necrosis.

38. The method of claim 36 wherein the antibody is an anti-ICAM-1 antibody.

39. The method of claim 38 wherein the anti-ICAM-1 antibody is R6.5 ATCC #HB9580.

40. The method of claim 36 wherein the animal is treated between three and six hours after the skin burn.

41. The method of claim 36 wherein the therapeutically effective amount of the antibody includes between about 1 mg/kg to about 3 mg/kg of the anti-ICAM-1 antibody or between about 1 mg/kg to about 3 mg/kg of the anti-CD18 antibody.

42. The method of claim 36 wherein the animal is a rabbit or a human.

43. The method of claim 36 wherein the pharmaceutically acceptable carrier solution is Ringers solution.

44. The method of claim 36 wherein the antibody is administered intravenously.

45. The method of claim 36 wherein the antibody is injected as a single bolus injection.

46. A method for treating a burn injury comprising administering about 10 mg/kg of an anti-ICAM monoclonal antibody to an animal having a burn injury.

47. The method of claim 46 wherein the monoclonal antibody is produced by a hybridoma ATCC #HB9580.

* * * * *